US011009470B2

(12) United States Patent
Yamakawa et al.

(10) Patent No.: US 11,009,470 B2
(45) Date of Patent: May 18, 2021

(54) X-RAY APPARATUS, DATA PROCESSING APPARATUS AND DATA PROCESSING METHOD

(71) Applicant: JOB CORPORATION, Kanagawa (JP)

(72) Inventors: Tsutomu Yamakawa, Kanagawa (JP); Shuichiro Yamamoto, Kanagawa (JP); Masahiro Okada, Kanagawa (JP)

(73) Assignee: JOB CORPORATION, Kanagawa (JP)

( * ) Notice: Subject to any disclaimer, the term of this patent is extended or adjusted under 35 U.S.C. 154(b) by 50 days.

(21) Appl. No.: 15/740,892

(22) PCT Filed: Oct. 24, 2016

(86) PCT No.: PCT/JP2016/081483
§ 371 (c)(1),
(2) Date: Dec. 29, 2017

(87) PCT Pub. No.: WO2017/069286
PCT Pub. Date: Apr. 27, 2017

(65) Prior Publication Data
US 2018/0214113 A1 Aug. 2, 2018

(30) Foreign Application Priority Data
Oct. 23, 2015 (JP) .............................. JP2015-209253

(51) Int. Cl.
G01N 23/04 (2018.01)
G01N 23/18 (2018.01)
(Continued)

(52) U.S. Cl.
CPC .............. G01N 23/04 (2013.01); A61B 6/00 (2013.01); A61B 6/584 (2013.01); G01N 23/083 (2013.01);
(Continued)

(58) Field of Classification Search
CPC ..... G01N 2223/3035; G01N 2223/612; G01N 2223/6126; G01N 2223/618; G01N 2223/652
See application file for complete search history.

(56) References Cited

U.S. PATENT DOCUMENTS 10,451,568 B2 * 10/2019 Moriyasu ............... A61B 6/032
2007/0237288 A1 * 10/2007 Tkaczyk ................ A61B 6/032
378/5

(Continued)

FOREIGN PATENT DOCUMENTS

JP 2002-291729 10/2002
JP 2006-101926 4/2006
(Continued)

OTHER PUBLICATIONS

Naser Rasoulpour et al., "A new approach for bean . . . local spectrum distributions", Nuclear Instruments and Methods in Physics Research A, 794 (2015), 177-184.
(Continued)

Primary Examiner — Christine S. Kim
(74) Attorney, Agent, or Firm — Clark & Brody LP

(57) ABSTRACT

Based on counts detected by a photon counting detector, a characteristic of X-ray attenuation amounts μt is acquired for each X-ray energy bin. This characteristic is defined by a plurality of mutually different known thicknesses t and linear attenuation coefficients in the X-ray transmission direction. This substance is composed of a material which is included in an object and which is the same in type as the object or which can be regarded as being similar to the object in terms of the effective atomic number. Correcting data for replacing the characteristic of the X-ray attenuation amounts μt by a linear target characteristic are calculated. The linear target characteristic is set to pass through the origin of a two-dimensional coordinate having a lateral axis
(Continued)

assigned to thicknesses t and a longitudinal axis assigned to the X-ray attenuation amounts $\mu t$. The correcting data are calculated for each X-ray energy bin.

24 Claims, 19 Drawing Sheets

(51) Int. Cl.
*A61B 6/00* (2006.01)
*G01N 33/10* (2006.01)
*G01N 23/087* (2018.01)
*G01N 33/02* (2006.01)
*G01N 23/083* (2018.01)

(52) U.S. Cl.
CPC ........... *G01N 23/087* (2013.01); *G01N 23/18* (2013.01); *G01N 33/025* (2013.01); *G01N 33/10* (2013.01); *G01N 2223/618* (2013.01); *G01N 2223/6126* (2013.01)

(56) References Cited

U.S. PATENT DOCUMENTS

| | | |
|---|---|---|
| 2011/0235773 A1 | 9/2011 | Baba |
| 2016/0089105 A1* | 3/2016 | Park .......................... A61B 6/02 378/54 |
| 2018/0235562 A1* | 8/2018 | Petschke .............. A61B 6/5205 |
| 2019/0021685 A1* | 1/2019 | Kojima .................... A61B 6/03 |

FOREIGN PATENT DOCUMENTS

| | | |
|---|---|---|
| JP | 2010-091483 | 4/2010 |
| JP | 2013-119000 | 6/2013 |

OTHER PUBLICATIONS

Watabiki et al., "Development of Dual-Energy X-Ray Inspection System", Anritsu Technical No. 87, Mar. 2012.

* cited by examiner

FIG.6
(A)
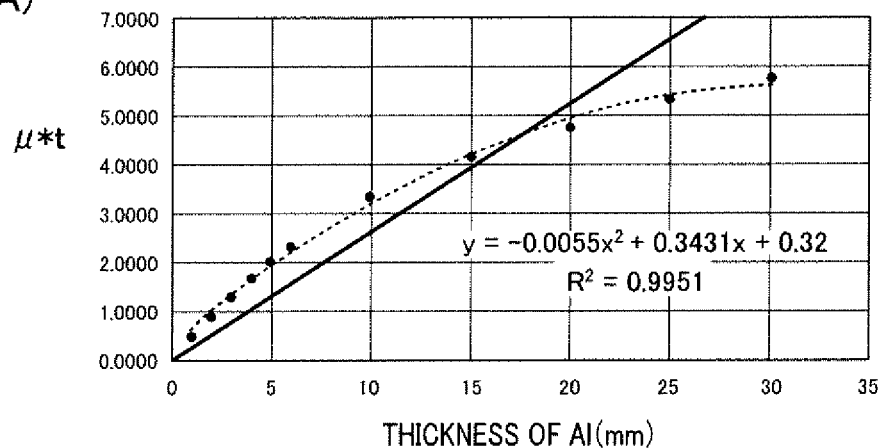
(B)
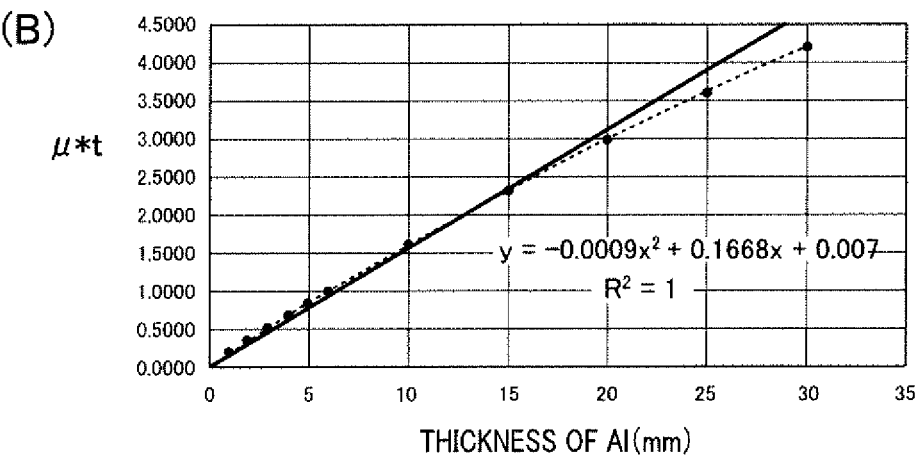
(C)
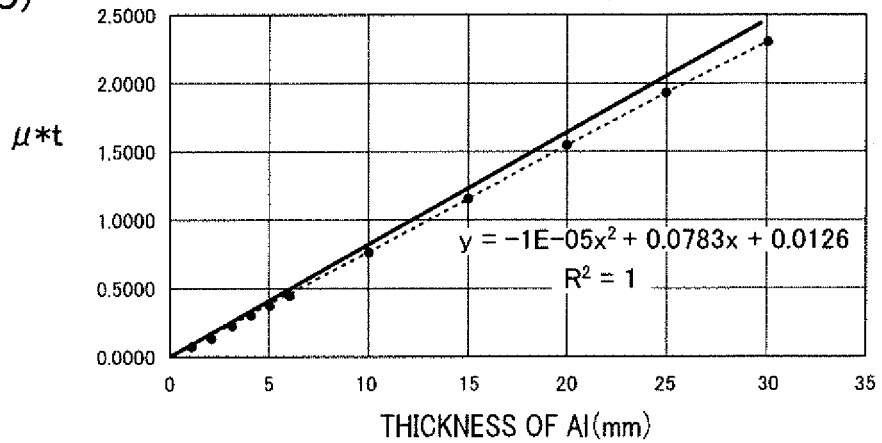

[THREE-DIMENSIONAL SCATTER DIAGRAM]

[ABSORPTION VECTOR LENGTH IMAGE]

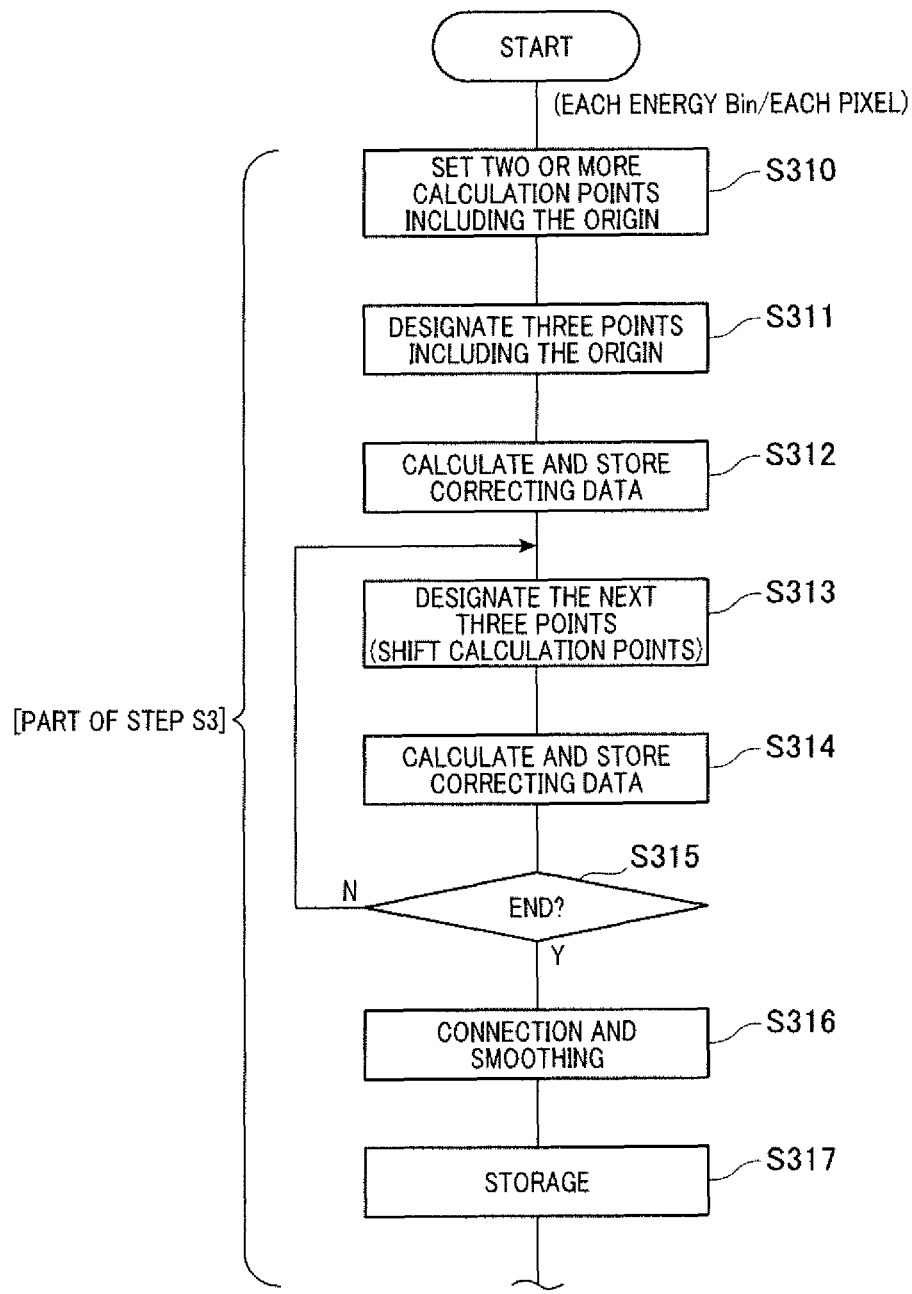

X-RAY APPARATUS, DATA PROCESSING APPARATUS AND DATA PROCESSING METHOD

CROSS-REFERENCE TO RELATED APPLICATION

This application is based on and claims the benefit of priority from earlier Japanese Patent Application No. 2015-209253 filed on Oct. 23, 2015, the description of which is incorporated herein reference.

TECHNICAL FIELD

The present invention relates to an X-ray apparatus that scans an object with X-rays to acquire X-ray transmission data and checks states of the object based on the acquired data, and a data processing unit which can be installed in the X-ray apparatus, and in particular, the X-ray apparatus which uses X-rays with a continuous energy spectrum and the data processing apparatus which can be installed in this X-ray apparatus.

BACKGROUND ART

In recent years, inspection using X-ray beams to check the internal state of an object has been widely used in various fields, such as foreign matter inspection of food, baggage inspection, and medical X-ray mammography.

For example, airports, public facilities, or the like use a content inspection that is an inspection of the types and shapes of baggage or mail contents, which is carried out without opening the baggage or mail. It is desired that such a content inspection should find out the presence of foreign matters (for example, metal pieces), if mingled into known types of objects (for example, food such as bread), and specify the types of the foreign matters. In other words, there is a potentially higher need for determining the types and/or shapes of objects (materials) by using X-rays.

For such needs, for example, there is proposed a technique as set forth in a patent publication 1 (JP-A-2010-091483, title of the invention is a "method and apparatus for inspecting foreign matters"). This patent publication 1 is based on an inspection technique called a dual energy technique (or a subtraction technique). This inspection technique uses the fact that two types of X-rays of energy (that is, two types of X-rays having different wavelengths) penetrating a substance arises a difference therebetween in X-ray transmission information. Practically, this inspection technique uses the following processing. First, two types of X-ray images based on lower X-ray energy and higher X-ray energy are made simultaneously, and a difference between the images is calculated. Then, from the resultant image difference, image components of a mingled foreign matter are extracted. The image components are then subjected to threshold processing to detect the foreign matter.

In the patent publication 1, optimum parameters for the difference calculation are set automatically, in addition to performing the foregoing basic process, to detect foreign maters at higher sensitivity. The patent publication 1 suggests use of a detector capable of detecting incidence of X-ray photons, with X-ray photon energy being discriminated. In other words, as a measure to simultaneously obtain two types of X-rays having lower energy and higher energy, the patent publication 1 suggests use of a well-known photon-counting X-ray radiation and detection system.

There is known another inspection method based on the foregoing dual energy technique as described in a non-patent publication 1. This non-patent publication 1 provides a detecting system using a basic configuration for the dual energy technique. With this configuration, an overlap of objects on the conveyance belt is ensured not to be mistakenly taken as foreign matters, so that foreign matters are detected with higher sensitivity.

When using the dual energy technique described in the patent publication 1 and the non-patent publication 1, an object or foreign matters mingled into the object may be detected with sensitivity that is improved to some extent. The term "improved to some extent" means that the detection sensitivity is improved if imaging conditions and/or image processing conditions are narrowed to specific conditions. Thus, detection conducted under such specific conditions limits imaging objects or imaging conditions to which the technique is applied, that is, narrows the conditions for detecting foreign matters.

Specifically, the dual energy technique described in these publications offers accuracy that is so low as not to reflect the difference in attenuation degree of the X-ray photon energy and materials, and gives little consideration to the electric noise or nonlinear characteristics of X-ray detection circuits, which may be unignorable problems. Accordingly, it is mostly difficult to detect the types or natures of foreign matters. This means that it is difficult to identify the types or natures of the materials the X-rays penetrate.

A patent publication 2 offers a proposal for eliminating such inconveniences. This proposal is based on a method of using an image acquired such as from a tomography apparatus which makes use of laminography. Using the acquired image, the type of the material contained in an object is easily identified with good accuracy. Specifically, in the method, the X-ray energy is discriminated into a plurality of energy regions to count photons in the regions, followed by reconstituting the image of the object using the counts. Then, based on the reconstituted image, the material that is present in a portion of interest in the object is identified. With this method, a reference image is produced based on the counts obtained from an image of the material where the thickness and the density are uniform. Then, the pixel value of the object image is divided by the pixel value of the reference image, for each pixel, to standardize the pixel value of the object image. Based on the standardized pixel values, a scatter diagram is prepared. In the scatter diagram, one axis of the two dimension is designated with absorption information, and the other axis thereof is designated with beam-hardening information of the X-rays. Identification information is acquired from the scatter diagram to identify the type of the material present in the imaged portion of the object.

CITATION LIST

Patent Publication 1] JP-A-2010-091483
Patent Publication 2] JP-A-2013-119000
Non-patent Publication 1]
"Development of dual-energy X-ray foreign matter detector", No. 87, March 2012, Anritsu Technical The material identification method described in the patent publication 2 needs to obtain a scatter diagram. Use of such a scatter diagram is convenient for visually finding information on the mingling of materials. Information on energy BIN is obtained in this method by calculating a value on the beam-hardening axis through a division process of the original image. This way of obtaining the information may be the cause of increasing noise. In addition, since this method defines no pass point for least squares (pass point such as a requirement of passing a coordinate origin), the approximation error, if any, may be large and thus the results are unlikely to be stable. Furthermore, in this method, not all of the collected data are used for preparing the scatter diagram.

When the material identification method described in the patent publication 2 is applied to an oral cavity as exemplified, X-rays penetrate the hard tissues, such as the teeth or the jaws. In this case, the effective energy of the X-ray energy bins may depend on the thickness of the object due to the influence of beam hardening. In particular, the variation depending on the thickness is more prominent in the X-ray energy bins toward lower energy side. Accordingly, the material identification method described in the patent publication 2 exerts its effects if at least the thickness information is correctly acquired. Otherwise, the identification accuracy may be low because the effect such as of beam hardening is unignorable.

SUMMARY

Thus, it is desired to provide an X-ray apparatus that can obtain signals as a result of eliminating or alleviating the influence of X-ray attenuation due to physical phenomena, such as beam hardening, for each X-ray energy BIN by using counts that are each derived from a photon-counting type detector, and can enhance the accuracy and reliability of various processes in which the signals are used, an object of providing a data processing apparatus and a data processing method which are favorably applied to the X-ray apparatus, and an object of identifying or estimating natures of a material based on the resultant data, or accurately detecting foreign matters or lesions, or estimating weight or thickness.

In order to accomplish the foregoing objects, as one mode of the present disclosure provides an X-ray apparatus which inspects an object, wherein beam-shaped X-rays having a preset continuous X-ray spectrum are radiated to an object and the object is inspected with the X-rays transmitted through the object. The X-ray apparatus includes a photon counting detector outputting a count by detecting the X-rays transmitted through a substance and measuring a count of number of photons of the X-rays in each of one or more X-ray energy bins which are set in advance, the substance being the same in type as the object or consisting of materials which are regarded as being similar in an effective atomic number to the object; characteristic acquiring means for acquiring a characteristic showing X-ray attenuation amounts $\mu t$ based on the count outputted from the detector in each of the X-ray energy bins, the X-ray attenuation amounts $\mu t$ being defined by mutually different known thicknesses t of the object in a transmission direction of X-ray fluxes of the X-rays and linear attenuation coefficients $\mu$ of the object; and correcting data calculating means for calculating, for each of the X-ray energy bins, correcting data, the correcting data replacing a characteristic of the X-ray attenuation amounts $\mu t$ acquired by the characteristic acquiring mean, with a linear target characteristic passing an origin of a two-dimensional coordinate system, the coordinate system having two axes which are mutually perpendicular, one of the axes being given to the thicknesses t and the other of the axes being given to the X-ray attenuation amounts $\mu t$.

In the present disclosure, the effective atomic number is defined as an average atomic number Zeff of an object which is composed of a plurality of substances (materials). "A substance which is the same in type as an object" is made reference to a substance having the same components as those of the object (i.e., the same type of object). Further, "a material which can be regarded as being similar to the object in terms of the effective atomic number" is, for example, according to acknowledge of the inventors, "a material has an effective atomic number belonging to a range of ±5 of an effective atomic number of the object." Preferably, it can be defined as "the material has an effective atomic number belonging to a range of ±2 of an effective atomic number of the object." In particular, in a case where it is desired to identify types and/or properties of substances inside an object at higher accuracy (for instance, when it is desired to have, with precision, a mammary gland content rate in mammography), the effective atomic number is set to the ±2 range. Such a substance is typically provided in the form of a phantom imitating the compositions of an object.

In the foregoing configuration, by way of example, the detector is provided with a plurality of pixels receiving incidence of the X-rays and is configured to detect the X-rays transmitted through the object at the respective pixels and count the number of X-ray photons at the respective pixels and in the respective one or more X-ray energy bins to output the count; the characteristic acquiring means is configured to acquire, based on the count outputted from the detector, the characteristic showing the X-ray attenuation amounts $\mu t$ in the respective X-ray energy bins and at the respective pixels or at respective pixel areas each consisting of two or more pixels; and the correcting data calculating means is configured to calculate the correcting data in the respective X-ray energy bins and at the respective pixels or at the respective pixel areas.

Further, the apparatus may include correcting means for correcting the count based on the correcting data in the respective X-ray energy bins and at the respective pixels or at the respective pixel areas.

Furthermore, the apparatus may include processing means for processing data for the inspection of the object based on the count corrected by the correcting means.

According to another mode of the present disclosure, there is provided a data processing apparatus installed in an X-ray apparatus which inspects an object, wherein beam-shaped X-rays having a preset continuous X-ray spectrum are radiated to an object, the X-rays transmitted through the object are detected to measure a count of photons of the X-rays in each of previously set one or more energy bins, and the count is outputted. The data processing apparatus includes characteristic acquiring means for acquiring a characteristic showing X-ray attenuation amounts $\mu t$ based on the outputted count in each of the X-ray energy bins, the X-ray attenuation amounts $\mu t$ being defined by mutually different known thicknesses t of the object in a transmission direction of X-ray fluxes of the X-rays and linear attenuation coefficients $\mu$ of the object; and correcting data calculating means for calculating, for each of the X-ray energy bins, correcting data, the correcting data replacing a characteristic of the X-ray attenuation amounts $\mu t$ acquired by the characteristic acquiring mean, with a linear target characteristic passing an origin of a two-dimensional coordinate system, the coordinate system having two axes which are mutually perpendicular, one of the axes being given to the thicknesses t and the other of the axes being given to the X-ray attenuation amounts $\mu t$.

Another mode of the present disclosure provides a data processing method performed in an X-ray apparatus which inspects an object, wherein beam-shaped X-rays having a preset continuous X-ray spectrum are radiated to an object, the X-rays transmitted through the object are detected to measure a count of photons of the X-rays in each of previously set one or more energy bins, and the count is outputted. The method includes steps of acquiring a characteristic showing X-ray attenuation amounts μt based on the outputted count in each of the X-ray energy bins, the X-ray attenuation amounts μt being defined by mutually different known thicknesses t of the object in a transmission direction of X-ray fluxes of the X-rays and linear attenuation coefficients μ of the object; and correcting data calculating means for calculating, for each of the X-ray energy bins, correcting data, the correcting data replacing a characteristic of the acquired X-ray attenuation amounts μt, with a linear target characteristic passing an origin of a two-dimensional coordinate system, the coordinate system having two axes which are mutually perpendicular, one of the axes being given to the thicknesses t and the other of the axes being given to the X-ray attenuation amounts μt.

A further modification is provided such that acquiring the characteristic and calculating the correcting data can be performed for each of the X-ray energy bins and at each of the pixels or at each of pixel areas each being composed of two or more pixels. In addition, acquiring the characteristic and calculating the correcting data can be applied to a signal detected by a detector (or sensor) having only one pixel or a signal detected by an X-ray spectrometer. The X-ray energy bins can be set after the signal acquisition, not limited to setting the bins before acquiring the signal.

Beam-shaped X-rays having a preset continuous X-ray spectrum are radiated to an object, and transmitted amounts of the X-rays are counted, as the number of X-ray photons (count), by a detector in each of one or more X-ray energy bins, so that the counts are detected. Based on the counts, in every X-ray energy bin, a characteristic of X-ray attenuation amounts μt is acquired before or during an X-ray examination. This characteristic is defined by a plurality of mutually different known thicknesses t of a substance which is the same in type as an object and linear attenuation amounts μ of the object. The thicknesses are taken in the X-ray transmitted direction. As a modification, the characteristic of X-ray attenuation amounts μt can be replaced by that of a substance composed of materials which can be regarded as being approximated to that of an object.

Correcting data for replacing, by a linear target characteristic, the acquired characteristic of X-ray attenuation amounts μt are calculated for each X-ray energy bin. The linear target characteristic passes the point of origin of a two-dimensional coordinate system having a lateral axis to which the thicknesses t are given and a longitudinal axis to which the X-ray attenuation amounts μt are given. Based on the calculated correcting data, the count in each X-ray energy bin is corrected, for instance.

When the X-rays having a continuous energy spectrum are radiated to an object, a distribution of counts which are outputs for X-ray energy amounts is influenced, more or less, by beam hardening and others. In this regard, however, the present disclosure, the correcting data for alleviating changes in the average (or effective) X-ray energy caused differently every X-ray energy bin and variations in comments of the X-ray energy.

Accordingly, using the correction data in correcting the measured values (counts) makes it possible to alleviate or remove the changes in the average (or effective) X-ray energy among the X-ray energy bins and variations in comments of the X-ray energy. This is thus substantially equivalent to radiation of monochromatic X-rays to an object, the monochromatic X-rays having an average (or effective) X-ray energy, which is for example a representative of each X-ray energy bin.

Hence, in detection of object-transmitted X-rays by the photon counting detector, influence on attenuation of the X-rays, which is caused by physical phenomena such as beam hardening can be removed or lessened, thus obtaining less-noise detection signals, thus improving accuracy and reliably of various processes which use such detection signals.

In addition, differently from use of the monochromatic X-rays, the continuous-spectrum X-rays are radiated, resulting in an increase in the number of detected X-ray photons, whereby S/N is also improvised.

Particularly, in applying the X-ray apparatus according to the present disclosure to an X-ray foreign-matter inspection apparatus which adopts a detector with two or more pixels, it is possible to check a substance composition in a wider area of the object. Instead, even if only one pixel is provided in the detector or an X-ray spectrometer is used, the X-ray apparatus is advantageous to checking a substance configuration and/or a property thereof in a narrower area of the object.

BRIEF DESCRIPTION OF THE DRAWINGS

In the accompanying drawings:

FIG. 6 exemplifies simulated graphs, for each of the X-ray energy bins, which explain a relationship between thicknesses t and X-ray attenuation amounts μt, which show influence of the beam hardening and other factors about aluminum material

FIG. 19 is a partial flowchart explaining a part of processes performed by the processor, according to the fifth modification.

DETAILED DESCRIPTION OF THE INVENTION

Hereinafter, embodiments according to the present invention will now be described. A data processing apparatus according to the present invention is also installed in this X-ray apparatus in a functionally integrated manner.

First Embodiment

Referring to FIG. 1 to FIG. 12, a first embodiment of the X-ray apparatus (and the data processing apparatus) will now be described.

Figure 1:
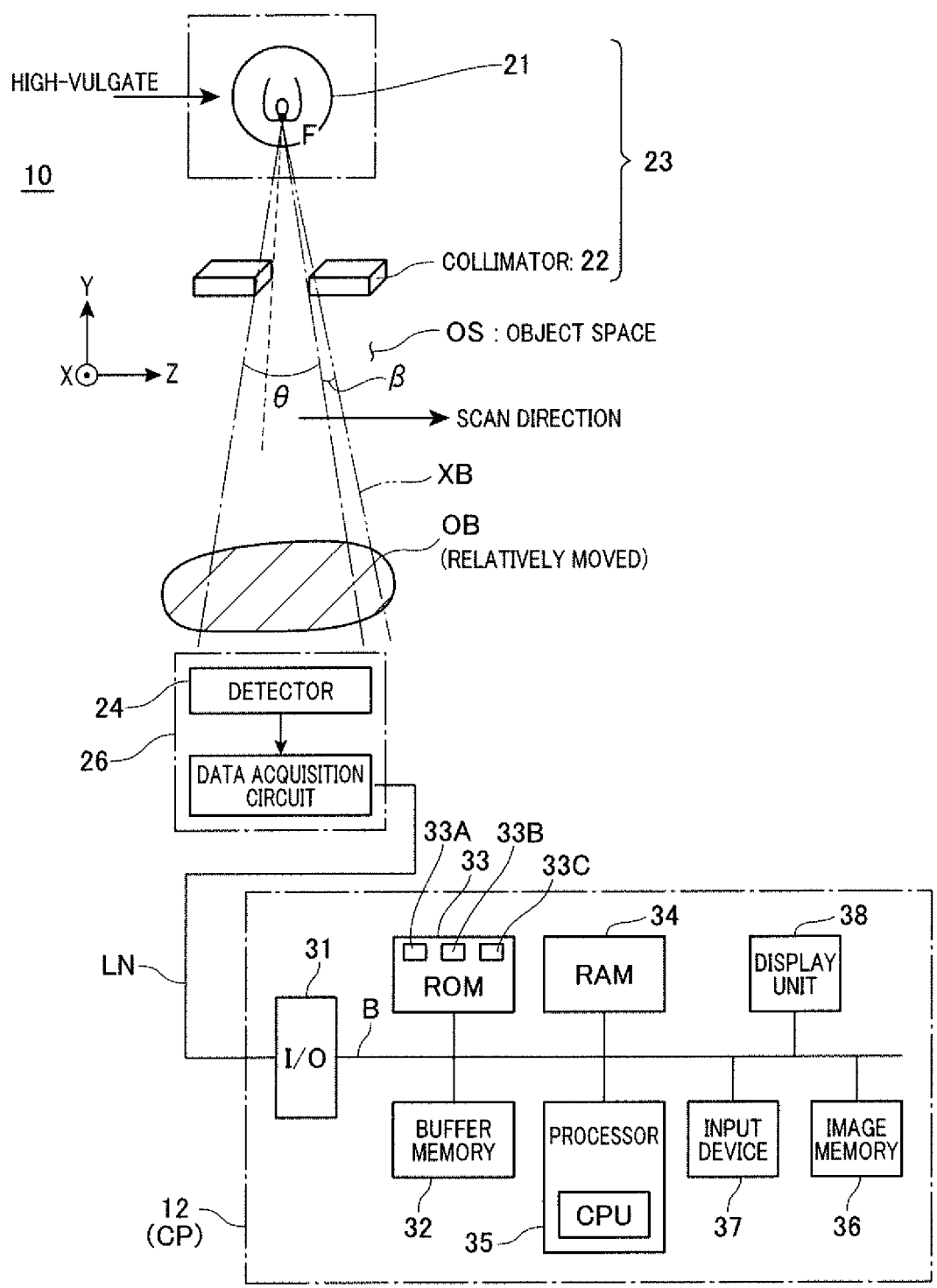
FIG. 1 is a block diagram outlining the configuration of an X-ray apparatus according to an embodiment of the present invention.

FIG. 1 outlines the X-ray apparatus provided according to the first embodiment. This X-ray apparatus can be provided as apparatuses for X-ray foreign-matter inspection or X-ray mammography. These apparatuses are directed to acquiring tomographic images and/or projected images of an object being inspected. In particular, the apparatuses can also be directed to inspecting whether or not foreign matter is attached to or misplaced inside an object (for example, a food item) and/or identifying (estimating, determining) the type and/or property of the foreign matter. The foreign matter is a substance other than materials composing a non-contained normal object. Such substances are metal pieces such as aluminum pieces or insects such as cockroaches. An apparatus to check existence of foreign matter is known as an X-ray foreign-matter inspecting apparatus. The X-ray apparatus of this embodiment is intended to perform an inspection to identify the type or property (or physical state) of foreign matter, that is, material (substance) identification, if there is known existence of the foreign matter.

An apparatus for the material identification is already known for example by JP-A 2013-119000 publication (title of the invention: Substance identification apparatus and substance identification method) and WO 2014 181889 (A1) publication (application number: PCT/JP2014/062631, title of the invention: Substance identification device and substance identification method employing X-ray panoramic/CT photographing). In addition, the present inventors have proposed various improvements in this substance identifying technique (for example, JP application Nos. 2015-023446 and 2015-85551).

FIG. 1 shows an X-ray apparatus 10 provided with a basic configuration required by the foregoing various substance identifying apparatuses (including an X-ray mammographic apparatus to check the breast whether or not a lesion is present).

As shown in FIG. 1, the X-ray apparatus 10 includes, as its essential elements, an X-ray generator 23 equipped with an X-ray tube 21 generating X-rays having a continuous energy spectrum and a photon counting detector 24 counting the number of photons and being arranged to be opposed to the ray tube 21. To the X-ray tube 21, driving high-voltage is supplied from a not-shown X-ray high-voltage generator for X-ray radiation. A space S (i.e., object space) is provided between the X-ray tube 21 and the detector 24 and an object OB being inspected (or inspected object) is positioned in the space S. For inspecting the object OB, the pair of the X-ray tube 21 and the detector 24 and the object OB are relatively moved to each other. In an X-ray inspection apparatus to inspect the type or property of a substance included in an object being inspected, the object OB is an object itself. In this case, by way of example, the object OB is a human breast.

Figure 2:
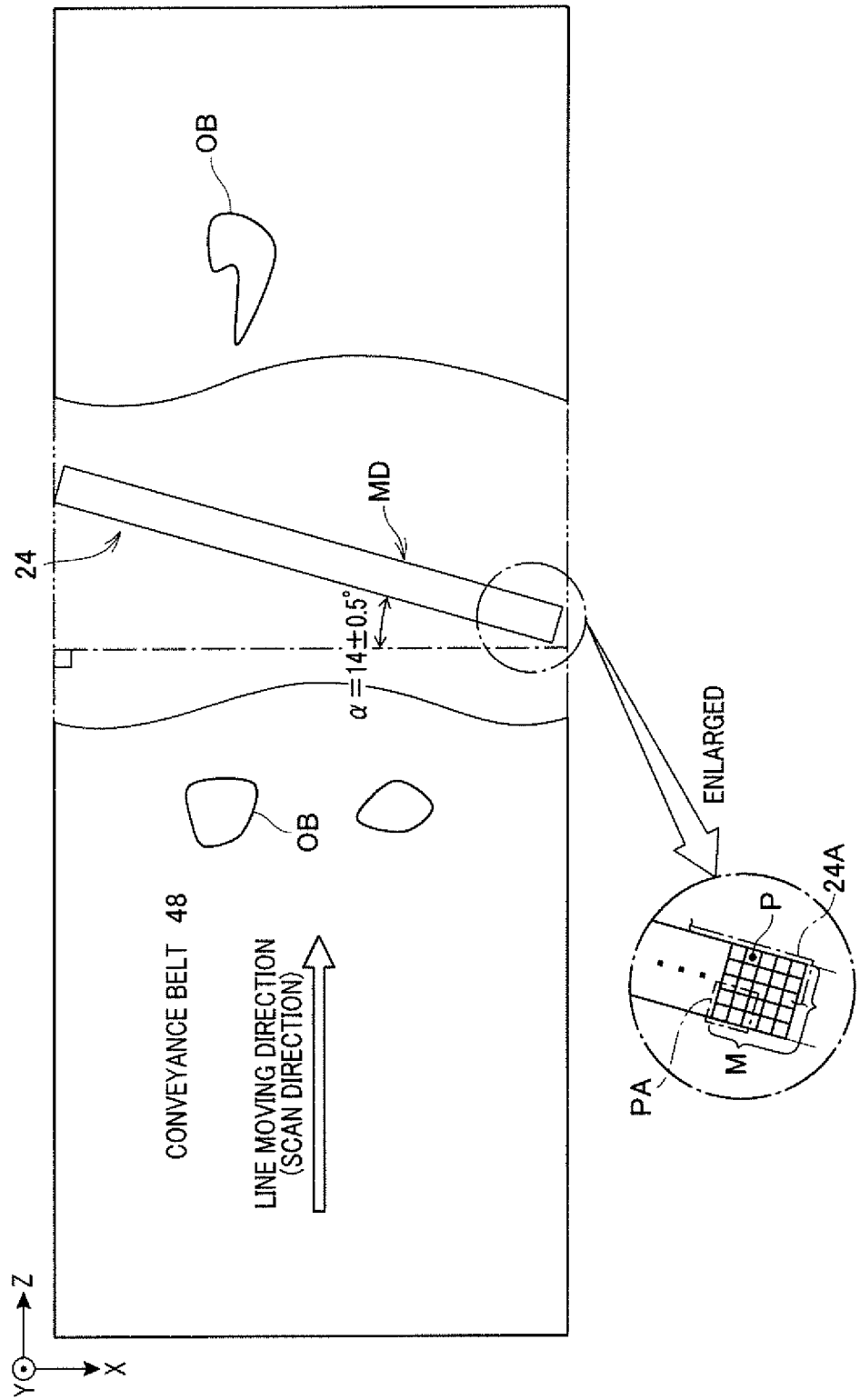
FIG. 2 is an illustration explaining a detector obliquely arranged in the X-ray apparatus according to the embodiment.

Further, for example, in an X-ray foreign-matter inspection which inspects a foreign matter which may present in (or outside, as attached thereon) an object (such as a food item or an industrial product whose component types are known), the object OB is placed on a conveyance belt 48 so as to pass through the object space S (refer to FIG. 2). Alternatively, it is possible to configured such that the object OB is located fixedly but the pair of the X-ray tube 21 and the detector 24 is moved around the object OB.

The X-ray tube 21 has a tube focal point F whose focal radius is 0.5 mmφ, for instance. Hence, the tube focal point F can be regarded as a substantial spot-shaped X-ray source. The X-rays emitted from the X-ray tube 21 are shaped, via a collimator 22, into a cone beam (or a fan beam) of X-rays. In FIG. 1, a cone-beam shaped X-rays XB is shown which has a cone angle θ and a fan angle β. In the configuration shown in FIG. 1, a Cartesian coordinate system with XYZ axes is provided, in which the Z-axis reaction is defined as a direction along which an object OB is moved in the object space S, which is thus referred to as a scan direction. The emitted X-rays XB are spread in a cone beam in the Y-axis direction which is along the height direction.

The cone-beam X-ray beam XB is transmitted through the object OB during which the beam is attenuated in its intensity, and the transmitted X-rays hits the detector 24. In an X-ray mammography, the pair of X-ray tube 21 and the detector 24 is rotated around a human breast is compressed by compression plates in a predetermined angular range.

As shown in FIG. 2, the detector 24 has an elongated shape in which a plurality of modules M (for example, 29 modules) arranged in sequence. In each module M, pixels P are two-dimensionally mapped in a matrix, such as 80×20 pixels, each having a pixel size of 0.2 mm×0.2 mm, for example. With this configuration, the foregoing X-ray incident window MD, which is approx. 47 cm in the longitudinal size and 0.4 cm in the lateral size, is formed as a detection layer 24A. The X-ray incident window MD provides 20×2348 pixels, for example. The plurality of modules M are aligned linearly, but in terms of pixel mapping, the detector 24 is configured as a direct conversion type of X-ray detector with an elongated shape, in which a plurality of pixels P exist even in the lateral direction. In the present embodiment, as will be detailed later, there is a configuration for correcting measured counts influenced by physical phenomena such as beam hardening. This correction can be performed for each of the pixels P as well as each virtual region virtually formed by grouping adjacently positioned actual pixels P. This virtual region is exemplified by a reference number PA shown in FIG. 2.

Under the conveyance belt 48, this detector 24 is arranged obliquely such that the longitudinal axis of the detector is skewed by a predetermined angle (e.g., approximately 14 degrees) in the scan direction of the object OB (or a direction perpendicular to the scan direction).

Each of the module M has the detection layer 24A made of a semiconductor material, such as CdTe or CZT, which serves as an X-ray detecting element converting directly from X-rays to electrical signals. Though not shown, on both sides of the detection layer 24A, charging and collecting electrodes are arranged for applying a high-voltage bias voltage between the electrodes.

Figure 3:
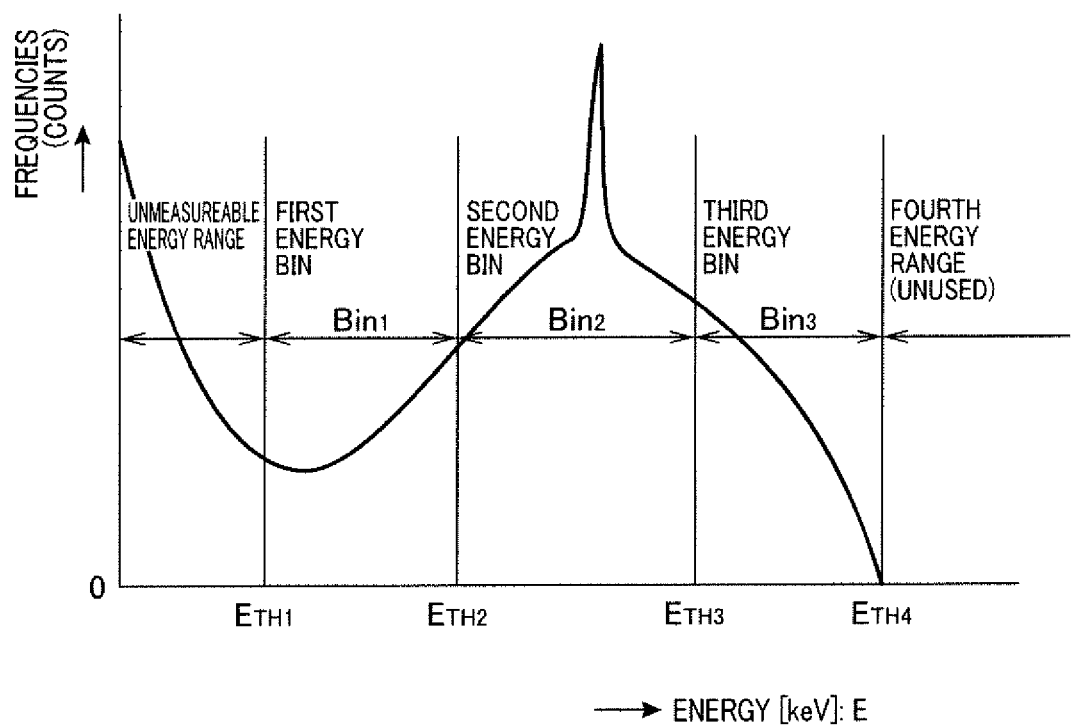
FIG. 3 is a graph explaining a spectrum of incidence of X-ray photons, in which a plurality of energy bins are set in the spectrum.

This detector 24 is a photon counting detector (a photon counting type of detector), which regards X-rays as an aggregate of photons having various energies and is capable of detecting of measuring the number of photons of the X-rays every energy bin. As shown in FIG. 3, the energy bins are set for example as three energy bins $Bin_1$ to $Bin_3$. The number of energy ranges is not limited to three, but may be one, or two or more which is other than three.

In the energy spectrum [keV], an energy range lower than a lower-limit threshold TH1 and an energy range upper than an upper-limit threshold TH4 (which is set to the tube voltage) are set as being an unmeasurable range and an unused range, respectively. The range between the thresholds TH1 to TH4 is divided into a single range (in this case, the thresholds are composed of only TH1 and TH4) or into a plurality of energy bins, BINs. For example, when thresholds TH2 and TH3 are set as shown in FIG. 3, there can be provided three energy bins, BINs.

In the detector 24, a layered data acquisition circuit 25 is formed, as a ASIC layer, beneath the detection layer 24A. With this formation, every pixel P and every energy bin, BIN, X-ray intensities are detected by the data acquisition circuit 25 as digital counts (accumulated amounts) indicating the number of photons at intervals. The detector 24 and the data acquisition circuit 25 configure a detection unit 26.

When a single photon hits a single pixel P, an electrical pulse signal is generated at the pixel P, of which signal wave height depends on the energy of the photon. The wave height value of the electrical pulse signal, that is, the energy amount, thus makes the count by one in an energy bin, BIN, to which the energy amount belongs. The count is thus collected by the data acquisition circuit 25, at every pixel P and in every energy bin, BIN, as accumulated values (digital values) measured at intervals.

By setting a sampling frequency to a higher value in the data acquisition circuit 25, the digital counts can be acquired from the respective ones of, for example, 20×2348 pixels at a frame rate of, for example, 6600 fps, at every pixel P and in every energy bin, BIN This direct conversion type of detector, together with the data acquisition circuit, is known and, for example, exemplified by a European patent publication No. 2674787.

The detector 24 is not always limited to the foregoing direct-conversion type configuration. One alternative to this detector 24 is a photon counting detector configured as a $CeLaCl_3$ detector, in which SiPM (or referred to as MPPC) is provide with micro column scintillators each of which has a diameter of several tens of micrometers.

The digital counts, which are repeatedly outputted at constant intervals from the data acquisition circuit 25 of the detection unit 26 at every pixel and in every energy bin, BIN, are sent as frame data to the next-stage data processing apparatus 12.

The data processing apparatus 12 can be installed as an apparatus integrated with the X-ray apparatus 10 or an inspection system. As in the present embodiment, the data processing apparatus 12 can be communicably connected to the X-ray apparatus 10 via a communication line LN. In this configuration, the line may be always-on connection or on-demand connection. In addition, the data processing apparatus 12 can be provided as a stand-alone type apparatus.

The data processing apparatus 12 is configured, by way of example, as a computer system CP. This computer system CP itself may be a computer system having known calculation functions, in which an interface (I/O) 31 is provided which is connected to the detection unit 26 via the communication line LN. To the interface 41, via inner buses B, a data processor 35 equipped with a buffer memory 32, a ROM (read-only memory) 33 (which foundations as a non-transitory computer readable medium), a RAM (random access memory) 34, and a CPU (central processing unit); an image memory 36; an input device 37; and a display unit 38 are communicably connected with each other via the buses.

The ROM 33 is provided to previously store therein computer-readable programs for correcting counts and identifying substances (materials), which enable the data processor 35 to read the programs and store them in its work area for execution. For this purpose, the ROM 33 is provided with a program storage area (functioning as a non-transitory computer recording medium) for previous storage of such programs. The ROM 33 is also provided with first and second data storage areas 33B and 33C (the first and second storage means) which stores therein data for correcting counts, i.e., calibration of the counts, which will be detailed later.

The processor 35 reads necessary programs from the program storage area 33A of the ROM 33 into its own work area. The processor 35 is a CPU dedicated to image processing. The buffer memory 32 is provided to temporarily memorize the frame data sent from the detection unit 26. The RAM is provided to temporarily memorize data required during processing of the processor 35.

The image memory 36 is provided to store therein various image data and various kinds of information processed by the processor 35. The input device 37 and the display unit 38 function as a man-machine interface with users, in which the input device 37 receives input information given by users and the display unit 38 presents images and other information under control of the data processor 35.

[Correction Process]

A correction process for photon counts (measured amounts) performed in a system, which involves radiation of X-rays having a continuous energy spectrum and X-ray detection based on photon counting detection, will now be described. The correction process, which is according to one of features of the present invention, is executed by the processor 35.

(Background)

First of all, the background of this correction for the counts will be described.

In recent years, there have been proposed many requests for identifying the type or shape of an object by using X-rays having a continuous energy spectrum. One such example, which can be seen in ensuring food safety, is an inspection of food items for checking whether the food items are contaminated with foreign matters The reason why the continuous-spectrum (polychromatic) X-rays are used in the present embodiment exists in the fact that it is difficult to realize such an inspection system which uses monochromatic X-rays, that is, X-rays having a particular energy, even though the monochromatic X-rays provide higher quantitative images and are controlled more easily if being possible to be realized. An apparatus for generating monochromatic X-rays needs an accelerator such as a synchrotron, so that usage of such an apparatus is limited in terms of various factors including higher cost, complex mounting, and output power.

In contrast, the continuous energy-spectrum X-rays are (i.e., polychromatic X-rays) can be generated by accelerating electrons with a higher voltage to be radiated to a target member, made of material such as tungsten or molybdenum, in the vacuum. That is, compared with generating the monochromatic X-rays, the polychromatic X-rays can be generated at overwhelmingly lower cost and in an easier mounting structure. However, it is true that imaging using such X-rays having a continuous energy spectrum sacrifices, more or less, a higher quantitative performance.

In particular, such a sacrifice is image quality, One of the factors greatly influencing the image quality is a beam hardening phenomenon (simply, referred to as beam hardening), The beam hardening is a phenomenon in which, in the event, an average (effective) energy amount is shifted to a higher energy side due to the fact that, when the continuous energy X-rays pass through a substance, X-rays having lower energies are absorbed in the substance more than X-rays having higher energies. When this beam hardening occurs, artifacts are generated in reconstructed images or pixel values of such images tend to lose their quantitative performance. More or less, the beam hardening depends on the depth of a substance in it degree (showing a larger amount of the beam hardening as the depth increases). It can be summarized such that the degree of the beam hardening result from differences in mutual interaction caused between molecules (atomics) of an object and X-ray phonons. Incidentally, factors influencing image quality by such physical phenomena include a heel effect resulting from an X-ray generator, besides the beam hardening phenomenon. The correction of counts in the present invention features alleviation of such influences caused due to the various physical phenomena once for all.

In addition, the correction of counts also contributes to correction of errors of the counts which are attributed to individual differences of circuits components and circuit substrates. Such errors include variations in gains of the respective circuits, variations of offsets, variations in linearity characteristics of respective circuits, and variations in charge sharing. It is general that these variations may be obstacles to higher-accurate data process (such as substance identification), but can be improved in the present embodiment.

The present inventors found that the beam hardening has influence depending on amounts of energy of the X-rays even within the range of each of the energy bins, BIN, to which an attention has not been paid so far. In order to improve this issue, a correction technique has been developed and provided by the inventors. Provided that the physical phenomenon is inherent to a substance, which is an object, and an apparatus being used, this correction technique can be regarded as a kind of calibration technique. From this point of view, data for the correction can be referred to as calibration data.

(Outline of Correction)

When the X-ray apparatus according to the present embodiment is exemplified as an X-ray foreign-matter inspection apparatus, it is usual that an object being inspected (for example, a food item such as peppers) can be regarded as being composed of known substances (for example, its major component is water). Moreover, in such an inspection, a foreign matter being inspected is also limited to, for example, a particular metal preciously set (for example, one or more types of metals including aluminum, glass, iron, and/or other materials). In consideration of this situation, the correction technique for counts in the present invention is performed for previously acquired correction data assigned to various known substances. The X-ray apparatus of the present invention thus provides a basic configuration for accomplishing processes necessary for the correction, which can be summarized below.

Figure 4:
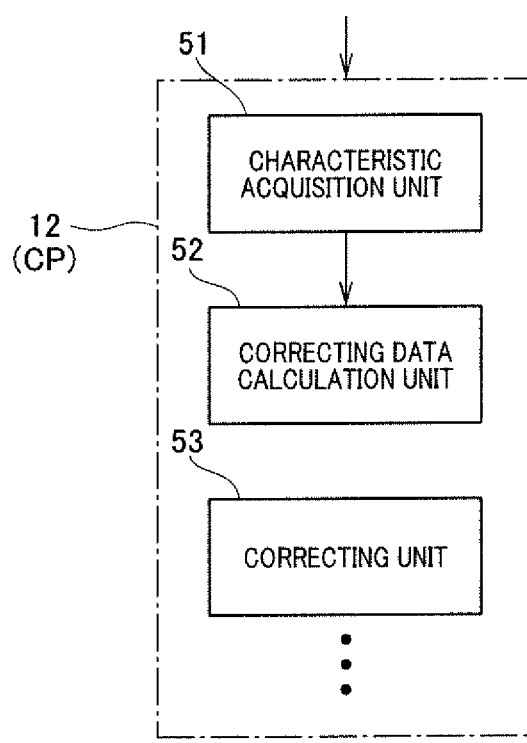
FIG. 4 is a block diagram explaining an outline of correction to influence of beam hardening or other factors, the correction being performed by a data processing apparatus.

As shown in FIG. 4, the basic configuration is provided with the data processing apparatus 12 in which a processor 35 plays central hardware which performs various software processes. Hence, in terms of the software or hardware, the data processing apparats 12 functionally includes a characteristic acquisition unit 51 and a correction data calculation unit 52. In addition, the data processing apparatus 12 can functionally be provided with a correcting unit 53.

These components 51 to 53 can thus be realized by software processes executed by the processor, i.e., the computer or by hardware circuits performing pipeline processes.

Of these components, the characteristic acquisition unit 51 is configured to acquire a characteristic of X-ray attenuation amounts μt defined by known mutually-different thicknesses t of a plurality of substances linear attenuation coefficients μ thereof, for each of the X-ray energy bins, BIN based on the counts outputted from the detector 24. The thicknesses are taken along a direction along which X-ray fluxes pass through the substances. The substances are similar in types to those composing an object or are regarded to be similar to materials of the substances in terms of X-ray linear attenuation coefficients. The correction data calculation unit 52 is configured to calculate, for each X-ray energy bin, BIN, correction data for replacing each of X-ray attenuation amounts μt acquired by the characteristic acquisition unit 51, with a linear target characteristic. This linear target characteristic is set as a linear line passing the origin of a two-dimensional Cartesian coordinate system (refer to FIG. 7 detailed later) provided with a lateral axis (one axis) assigned to thicknesses t and a longitudinal axis (the other axis perpendicular to the one axis) assigned to X-ray attenuation amounts μt.

The correcting data can be stored in a predetermined area of the ROM 33, thus making use of the correcting data by reading them from the ROM 33 when processing the counts. Alternatively, the correcting data can be obtained before performing an examination, between examinations, during an examination, or after finishing an examination. In addition, when once obtaining correcting data, the correcting data can be stored in a storage, and the stored correcting data can be subjected to update for the next use.

As a modification is that the foregoing characteristic acquisition and correcting data calculation are to be carried out in every X-ray energy bin, BIN, and at every pixel P or at every pixel area PA composed of a plurality of pixels P. Another modification is to carry out the foregoing characteristic acquisition and correcting data calculation with a detected signal from an X-ray detector or an X-ray senor, which is provided with only one pixel. Furthermore, the foregoing characteristic acquisition and correcting data calculation can be applied to a signal detected by an X-ray spectrometer (for example, EMF 123 type X-ray spectrometer produced by EMF Japan Co., Ltd.).

When the correcting unit 53 is provided in the X-ray apparatus, the correcting unit 53 is configured to correct the counts in each of the X-ray energy bins, BIN (or in each of the X-ray energy bins, BIN and at each of either the pixels P or the pixel areas PA) on the basis of the correcting data.

Hereinafter, how to correct the counts will now be described.

(Details of Correction Technique)

The present invention assumes a system in which X-rays having a continuous energy spectrum are radiated to an object, and X-rays transmitted through the object is discriminated into, for example, a plurality of energy bins, $Bin_1$ (i=1, 2, . . . ) in order to accomplish photon counting detection for the counts.

In this system, the characteristics of $\mu t$, which are calculated as a ratio between input and output photon counts in each X-ray energy bin, BIN ($\mu t = -\ln$(output count $Cl_i$/input count $Co_i$: i=1, 2, . . . )), are shifted from the linear line (i.e., target characteristics) each passing the origin of the foregoing coordinate system, depending on thicknesses t of substances of an object in the X-ray transmitted direction, thus providing characteristics different from those obtained when the object is subjected to radiation of monochromatic X-rays. The reasons for this shift includes the beam hardening and the heeling effect in each of the X-ray energy bins, BIN, and charge shearing occurring at pixels of the semiconductor detector, so that the present inventors have paid attention this shift. Measured X-ray attenuation amounts $\mu t$ are corrected with use of multiplication coefficients such that shifted curves of the X-ray attenuation amounts $\mu t$ agree with linear lines passing through the origin and having gradients=linear attenuation coefficients $\mu_{io}$ (i.e., constant values: not functions of the thickness t). These linear characteristics presenting the grading $\mu_{io}$ become target characteristics corresponding to monochromatic X-rays. By way of example, the target characteristic is set in each X-ray energy bin, BIN, and at each pixel.

The foregoing multiplication coefficients are data serving as the correcting data, and obtained previously using a calibration (correcting) phantom having a plurality of materials of which components are known and of which thicknesses are also known.

This phantom is made of the same substances as those composing an object or of substances composed of materials which can be regarded as being similar to the object in terms of an effective atomic number. The effective atomic number is defined as an average atomic number Zeff of an object when the object is made of a plurality of substances (materials) (for example, refer to Isotope News, issued August 2014, No. 724, "New X-ray imaging for visualizing the effective atomic number Zeff"). Additionally, "the same substances as an object" is defined as substances whose materials have the same composition (the same kind of materials). Moreover, according to a knowledge of the inventors, "the substances composed of materials which can be regarded as being similar to the object in terms of an effective atomic number" can be defined as materials having an effective atomic number falling into a range of ±5 of the effective atomic number of an object, for example. In particular, when it is desired to obtain, with accuracy, types and/or properties of substances (such as foreign matters) which may be contained in an object in actual imaging (for example, when it is desired to have, with precision, a mammary gland content rate in mammography), a knowledge has been obtained which it is desired to have a phantom whose materials have an effective atomic number falling into a range of ±2 of the effective atomic number of an object". For example, if an object has an effective atomic number of 7.2, it is desired that the phantom is composed of materials whose effective atomic number is 7.2±5, more desirably, 7.2±2.

The background of these numerical ranges will now be described by referring to a beam hardening correction which is necessary for material identification in the mammography. If the breast has no lesions, states of the beast can be expressed by a ratio of the mammary glands and fat. Hence, it is good if the beam hardening correction can be performed by a phantom having the same materials as tissues expressed by a 50% of mammary glands and a 50% of fat. However, it is actually diffident to obtain such a phantom, so that there is almost no option but to produce a phantom by combining ordinary generally-known materials. This time, for trying to conduct the beam hardening correction, the inventors made a phantom equivalent to a 50% of mammary glands and a 50% of fat, from breast-equivalent plate phantoms of XUR types made by KYOTO KAGAKU Co., LTD. The correction results were good. Meanwhile the inventors tried to make a aluminum phantom to conduct beam hardening correction for the breast, but it was difficult to obtain material identification with higher precision, because of dependency of the correction on tissue thicknesses. These experiments show that it is important to produce correcting data (i.e., calibration data) by using a phantom whose materials are similar to those of an object, which materials should be selected with consideration of the effective atomic number and to conduct the beam hardening correction using such correcting data.

First, as one example of previous measurement which uses the foregoing phantom, a relationship between respective X-ray energy bins and X-ray attenuation amounts will be explained in a case where the number of X-ray energy bins is three.

Figure 5:
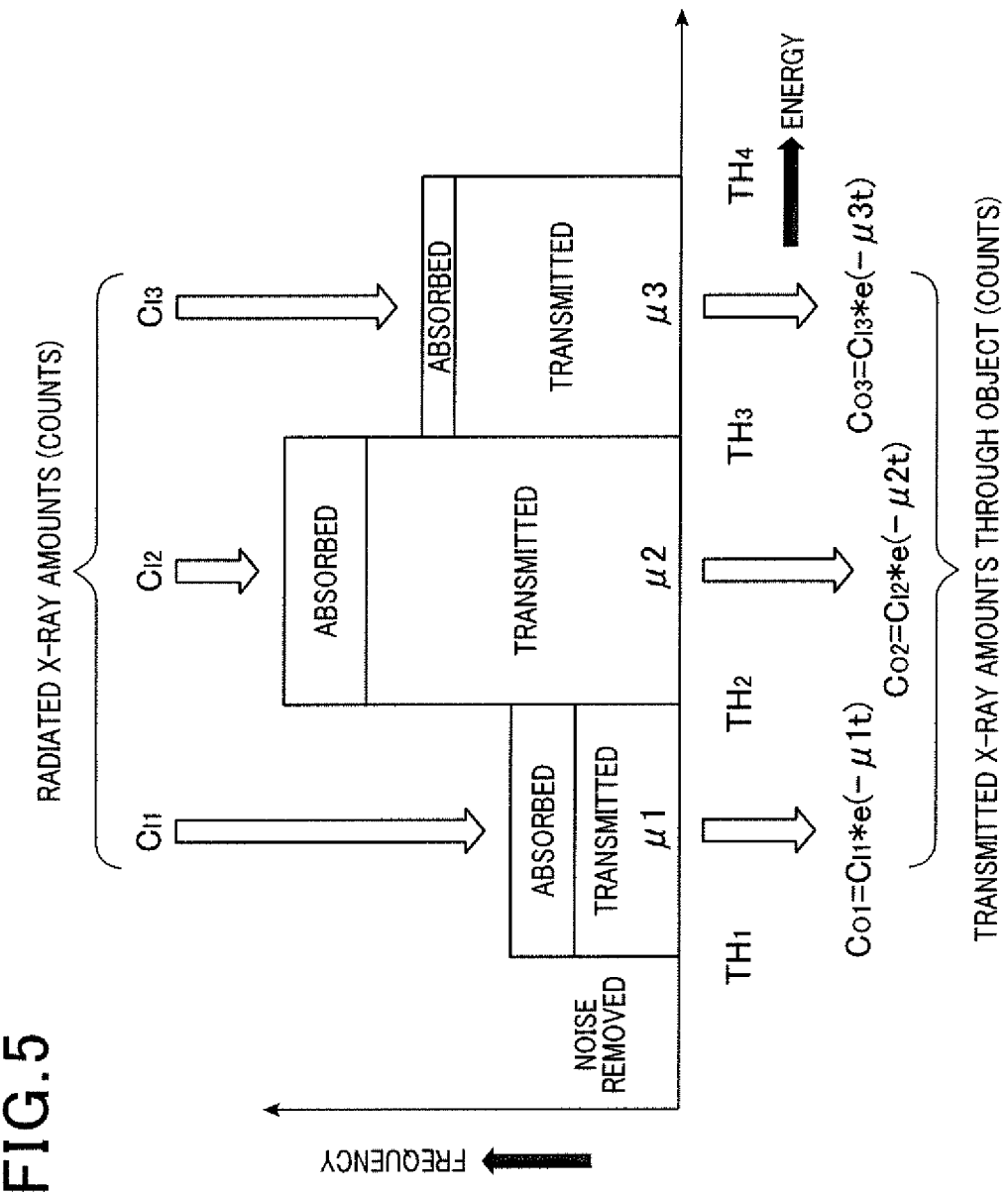
FIG. 5 is a graph explaining a relationship between incident amounts (counts) of the X-ray photons and transmitted amounts (counts: measured values) thereof in the respective X-ray energy bins.

As shown in FIG. 5, the X-ray energy bins, $Bin_1$ to $Bin_3$, shown in FIG. 3 are pictorially assigned to the lateral axis in FIG. 5 and measured values of X-ray photons counted in each of the X-ray energy bins, $Bin_i$ (i=1 to 3) is assigned, as counts, to the longitudinal axis. When an X-ray beam having a continuous energy spectrum is radiated, X-ray photons are absorbed and transmitted in and through an object in each of the X-ray energy bins, Bini, and the transmitted X-ray photons are detected. Assuming that the numbers of incident X-ray photons in the respective X-ray energy bins, $Bin_i$ are $Cl_1$, $Cl_2$, $Cl_3$ and the number of transmitted (emitted) X-ray photons are $Co_1$, $Co_2$, $Co_3$, the following expressions can be provided, $$Co_1 = Cl_1 \cdot e(-\mu_1 t)$$

$$Co_2 = Cl_2 \cdot e(-\mu_2 t)$$

$$Co_3 = Cl_3 \cdot e(-\mu_3 t),$$

wherein $\mu_1$, $\mu_2$, $\mu_3$ can be referred to as imaginarily-averaged linear attenuation coefficients in the respective X-ray energy bins, $Bin_i$ (in other words, linear attenuation coefficients provided to an effective energy amount in the respective energy bins). Meanwhile, the factor "t" is a depth (thickness) of the path in the X-ray transmission direction passing through the object. This case is premised on a condition that the imaginarily-averaged linear attenuation coefficients $\mu_1$, $\mu_2$, $\mu_3$ in the respective X-ray energy bins, $Bin_1$, are not dependent on the thickness t.

FIG. 6 shows actually measured results of the thicknesses t and imaginary attenuation values $\mu_i t$ (i=1 to 3) of aluminum (Al) adopted as a substance, under radiation of X-rays with a continuous-energy spectrum. In parts (A), (B) and (C) of FIG. 6, there are shown characteristics of the imaginary attenuation values $\mu_i t$ in the order of the lowest energy bin, $Bin_1$, an intermediate energy bin, $Bin_2$, and the highest energy bin, $Bin_3$. In these graphs, the linear characteristics show calculated values (i.e., theoretical values) of imaginary attenuation amounts $\mu_i t$ obtained when monochromatic X-rays having a central X-ray energy in each of the X-ray energy bins, $Bin_i$, are radiated. In contrast, when X-rays having a continuous energy spectrum are radiated, characteristics showing the imaginary attenuation amounts $\mu_i t$ are shifted from the linear characteristics, and degrees of their curves become larger in lower X-ray energy bins compared with higher X-ray energy bins. These curved characteristics can be approximated by quadratic curves. These curves show that the measured values are influenced by various factors, such as beam hardening which is a main factor, and the degree of such influence increases as an increase in the thickness t.

When the characteristics showing the attenuation amounts $\mu_i t$ shift from linear characteristics (corresponding to those obtained in radiation of monochromatic X-rays) passing the coordinate origin, scatter points also deviate from a certain range of distribution centering one point in a three-dimensional scatter diagram, which is provided from an object made of the same substances having different thicknesses. In other words, this means that the assumption that linear attenuation coefficients $\mu_i$ to the effective energies in the respective X-ray energy bins do not depend on the thicknesses is destroyed.

That is, this situation makes it difficult to estimate a distribution of scatter points or lower reliability of the estimation, which is required for substance identification (identifying, determining or estimating the type or property of a substance), which is a preferred example for the correction stated in the present embodiment.

(Acquisition of Correcting Data)

Hence, correcting data are previously set, which correct the shifted curves of the imaginary attenuation values so as to agree with the linear line (i.e., the linear target characteristic), which corresponds to that obtained in the radiation of designated monochromatic X-rays each of the X-ray energy bins. For example, the correcting data are set to be multiplication coefficients to correct the foregoing curves to linear lines each passing the coordinate origin.

Figure 7:
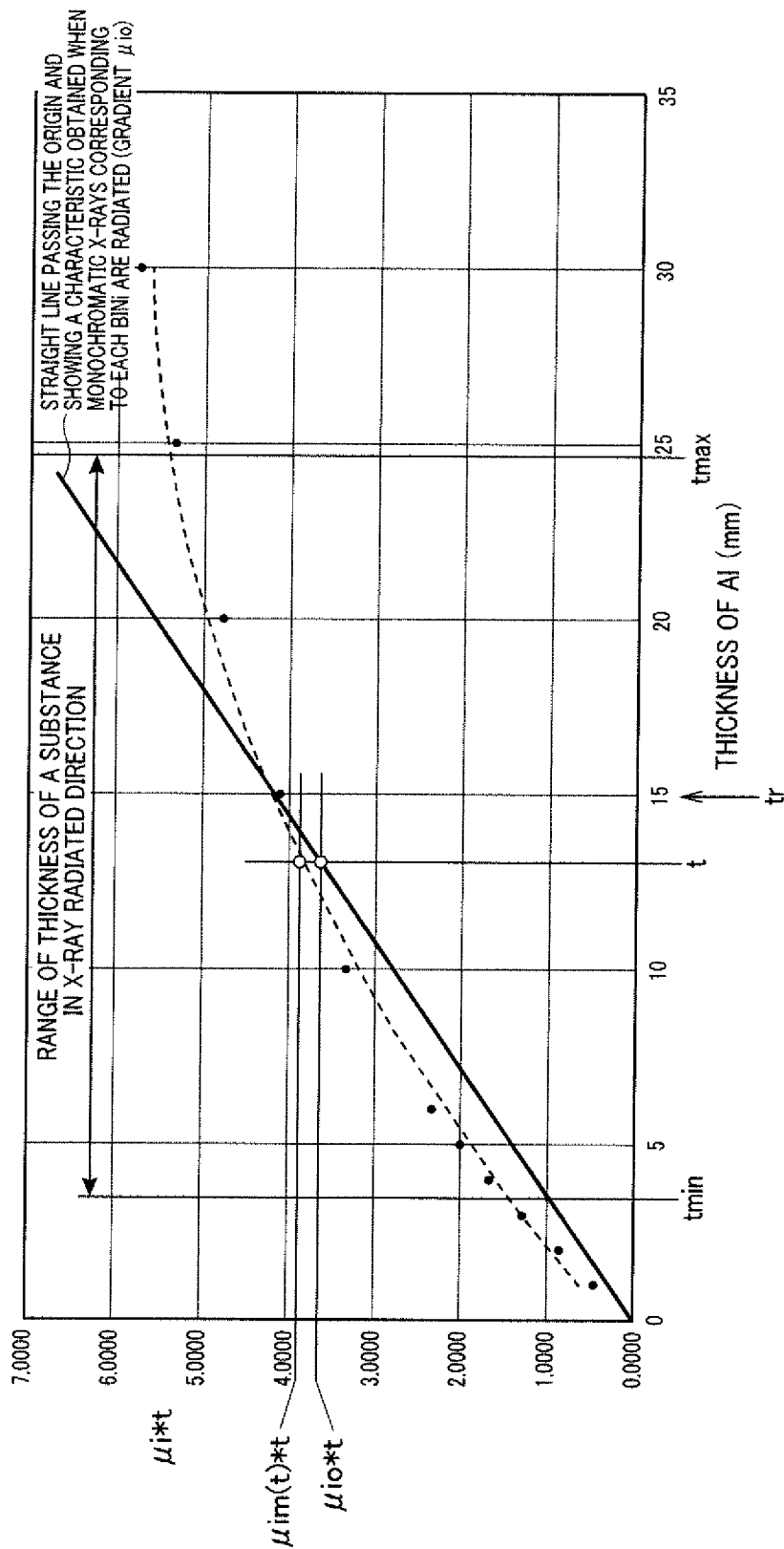
FIG. 7 is a graph explaining how to generate correcting data for correcting influence of the beam hardening and other factors.

Referring to FIG. 7, how to prepare for the correcting data in advance will now be described. The correcting data are acquired before an actual X-ray examination or X-ray imaging, and stored in the ROM 33, that is, storage means. When an examination or imaging is actually carried out, the correcting data are read from the ROM 33, and used to correct, at respective pixels P or pixel areas PA, measured values acquired in the form of frame data.

In FIG. 7, the longitudinal and lateral axes are given the same dimensions as those explained in FIG. 6(A) to (C) and are representative of such axes shown in FIG. 6(A) to (C). In this example, it is assumed that the substance is made of aluminum (Al). FIG. 7 exemplifies characteristics, in which a curve shows imaginary attenuation values measured at thicknesses t of the substance in the X-ray transmitted (projected) direction and a linear line shows imaginary attenuation values $\mu_i t$ (i=1 to 3) at the thicknesses t in the X-ray transmitted direction.

Of these characteristics, the linear line shows a characteristic of the imaginary attenuation values $\mu_i t$ obtained when monochromatic X-rays having an effective energy value in each of the X-ray energy bins, $BIN_i$ (i=1 to 3). This linear line passes through the origin of this two-dimensional coordinate at a gradient $\mu_{io}$, and can be obtained by approximate calculation applied to a curved line detailed later.

Meanwhile, the curved line exemplifies a characteristic obtained with the thicknesses t in the X-ray transmitted direction, when X-rays having a continuous energy spectrum (i.e., the polychromatic X-rays) are radiated to a substance made of aluminum. Since the polychromatic X-rays are used, the characteristic is curved, not along a straight line, due to the foregoing beam hardening or other physical factors. The characteristic shown by imaginary attenuation values $\mu_{it}$ for the polychromatic X-rays can be obtained, for example, by using a phantom having different portions whose thicknesses t are known and different from each other.

If it is assumed such that:

$\mu_i m(t)^* t$: an imaginary attenuation value calculated at a thickness t and in each of X-ray energy bins, $BIN_i$ ($\mu_i m$ indicates an imaginary linear attenuation coefficient and t indicates a thickness), $\mu_i o^* t$: a linear attenuation coefficient $\mu_{io}$ (not a function of t) corresponding to monochromatic X-rays at a thickness t in each of X-ray energy bins, $BIN_i$, and $C_i(t)$: multiplication-correcting coefficients for replacing the linear attenuation coefficients $\mu_{io}$ with those which do not depend on the thickness t, the multiplication-correcting coefficients $C_i(t)$ can be calculated based on:

$$\mu_i o^* t = C_i(t)^* \mu_i m(t).$$

Hence, the multiplication-correcting coefficients $C_i(t)$ are provided as correcting data.

Specifically, function forms which are candidates for one or more correction coefficients $C_i(t)$ are estimated, and any function form (for example, the quadratic function) is used for approximation of the curved characteristics. The correcting data $C_i(t)$ are then obtained, from the characteristics of the X-ray attenuation amounts $\mu_i m(t)^* t$ acquired at one or more thicknesses t, as a value which minimizes a value calculated based on the following expression:

$$\Sigma_{i\,min}^{i\,max}[(\mu_{im}(t) - \mu_{io})^2 \times t^2]$$

$(i=1,2,3)$

This expression involves tmin and tmax, which regulates a wide range which includes a lower value and an upper value of thickness of an object in the X-ray flux transmitted direction. The tmin and tmax can be set imaginarily when the object is examined.

The resultant correction data $C_i(t)$ calculated for the respective thicknesses t are stored in the first data storage area 33B of the ROM 33. Additionally, approximated data showing the foregoing function form (for example, the quadratic function) are also stored in the second data storage area 33C.

(Phantom)

Hence, in the present embodiment, various phantoms are use to previously measure (previous measurement) the imaginary attenuation values $\mu_i m(t)^* t$ shown in FIG. 7, at every pixel, so that the foregoing correcting data Ci(t) can be obtained at every pixel.

Figure 8:
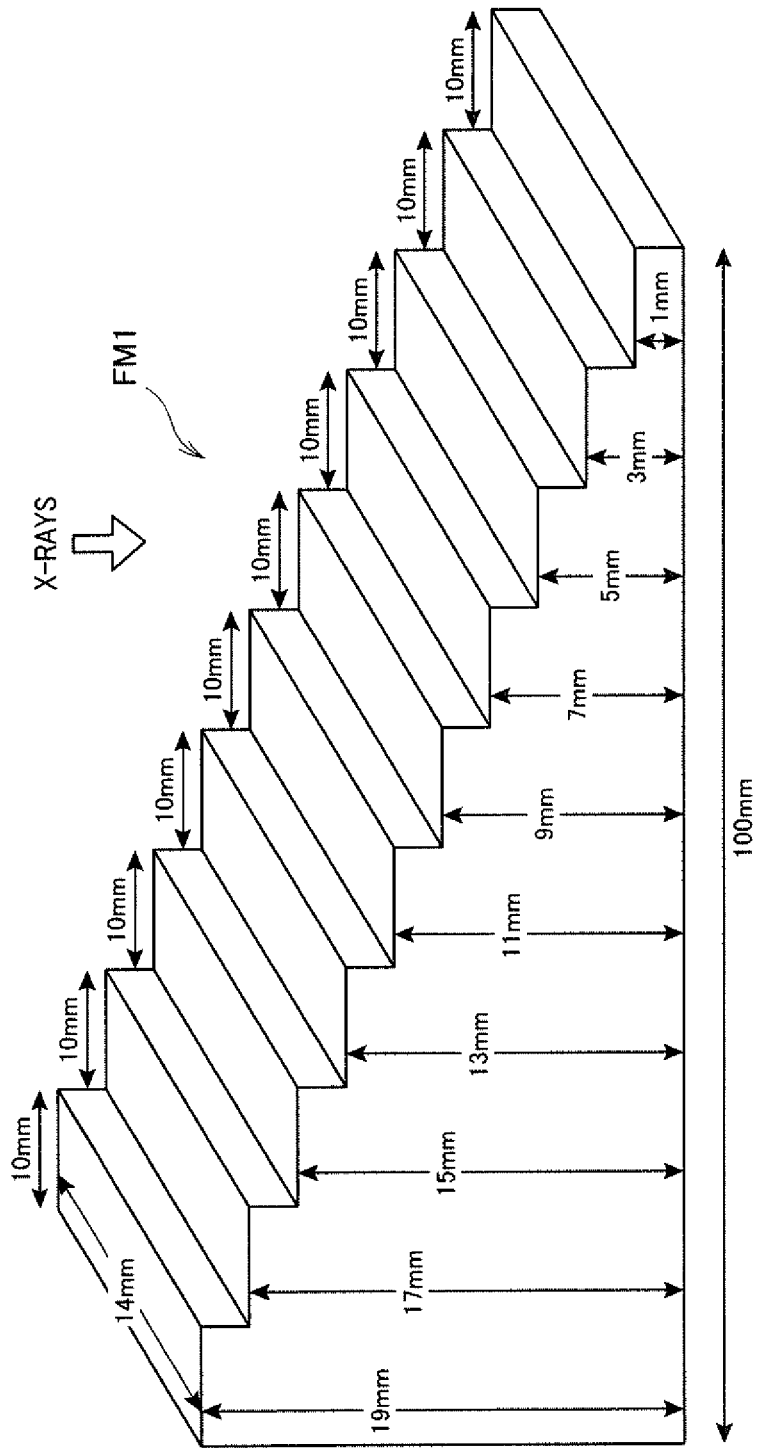
FIG. 8 is a perspective view exemplifying a phantom (calibration phantom) made of a known substance or a material imitating the known substance, the phantom being formed to have a plurality of steps having known thicknesses and being used for previously acquiring the correcting data.

As phantoms, various phantoms are used, which are composed of known type of substances (such as a water phantom imitating a pepper or an aluminum phantom imitating aluminum). FIG. 8 pictorially exemplifies a pepper phantom FM1, which can be used in an X-ray foreign matter inspection for inspecting whether peppers being inspected as food contain with foreign matters such as metals (such as aluminum). As a main component of the peppers is water, the phantom FM is provided as a container with water filled in, in which the container is a higher X-ray transmission rate. This phantom is structured to have portions whose heights correspond to thicknesses t (t=1 mm to 19 mm) changing stepwise in the X-ray transmission direction. This range of the thicknesses t is decided to cover possible material thicknesses of the peppers during the foreign matter inspection. Further, as to a phantom imitating foreign matter which may be contained in objects such as food items, it is ordinary that the foreign matter is smaller than the objects. As a result, in the case of the aluminum phantom, it is sufficient that the two or more stepwise portions have known thicknesses slightly changed step by step and the minimum and maximum thicknesses are also smaller.

Figure 9:
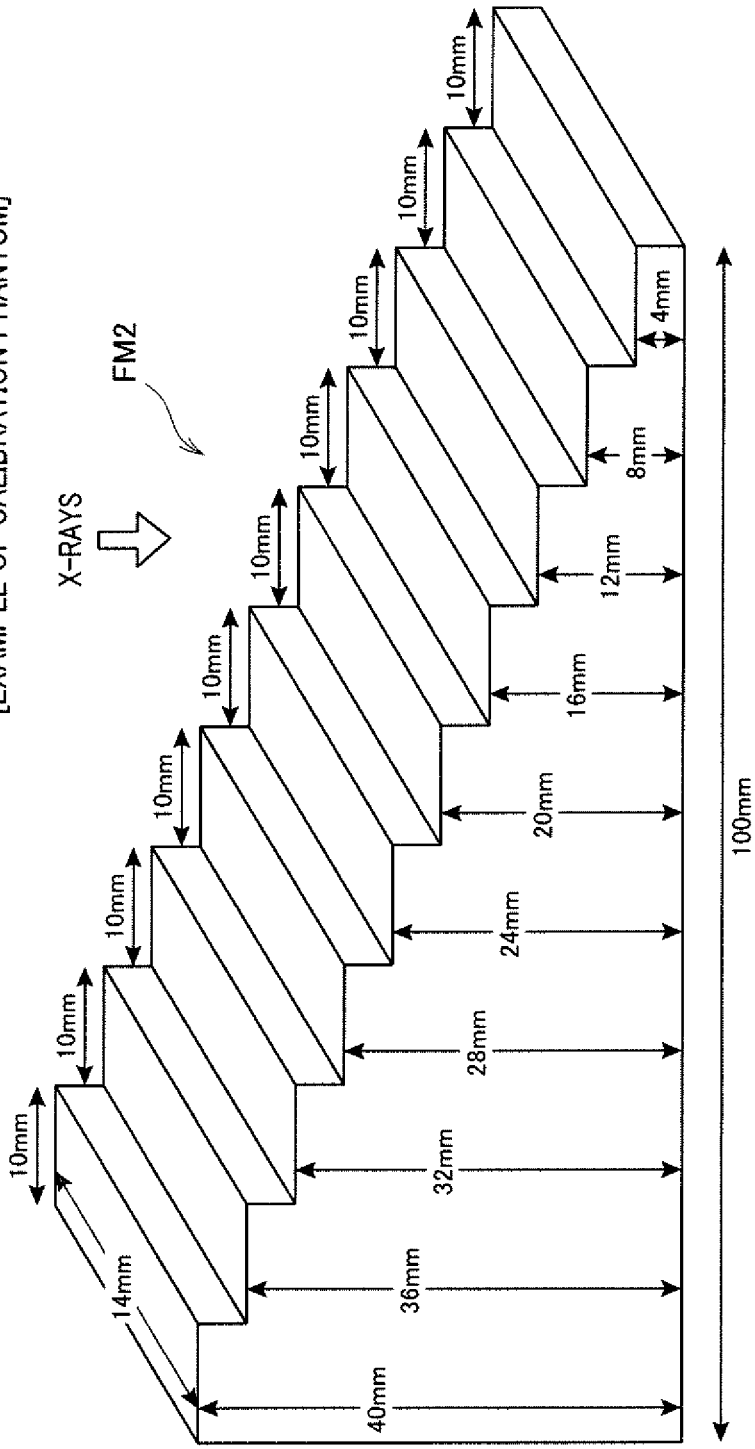
FIG. 9 is a perspective view exemplifying another phantom (calibration phantom) made of a known substance or a material imitating the known substance, the phantom being formed to have a plurality of steps having known thicknesses and being used for previously acquiring the correcting data.

FIG. 9 exemplifies another phantom FM2, which has a mixture of human muscle and adipose 70%. This phantom FM2 has different portions whose heights are set to cover actually supposed inspection thicknesses, so that, by way of example, there is step-wise structure whose heights change from 4 to 40 mm, at every 4 mm step.

(Example of Whole Processing)

Figure 10:
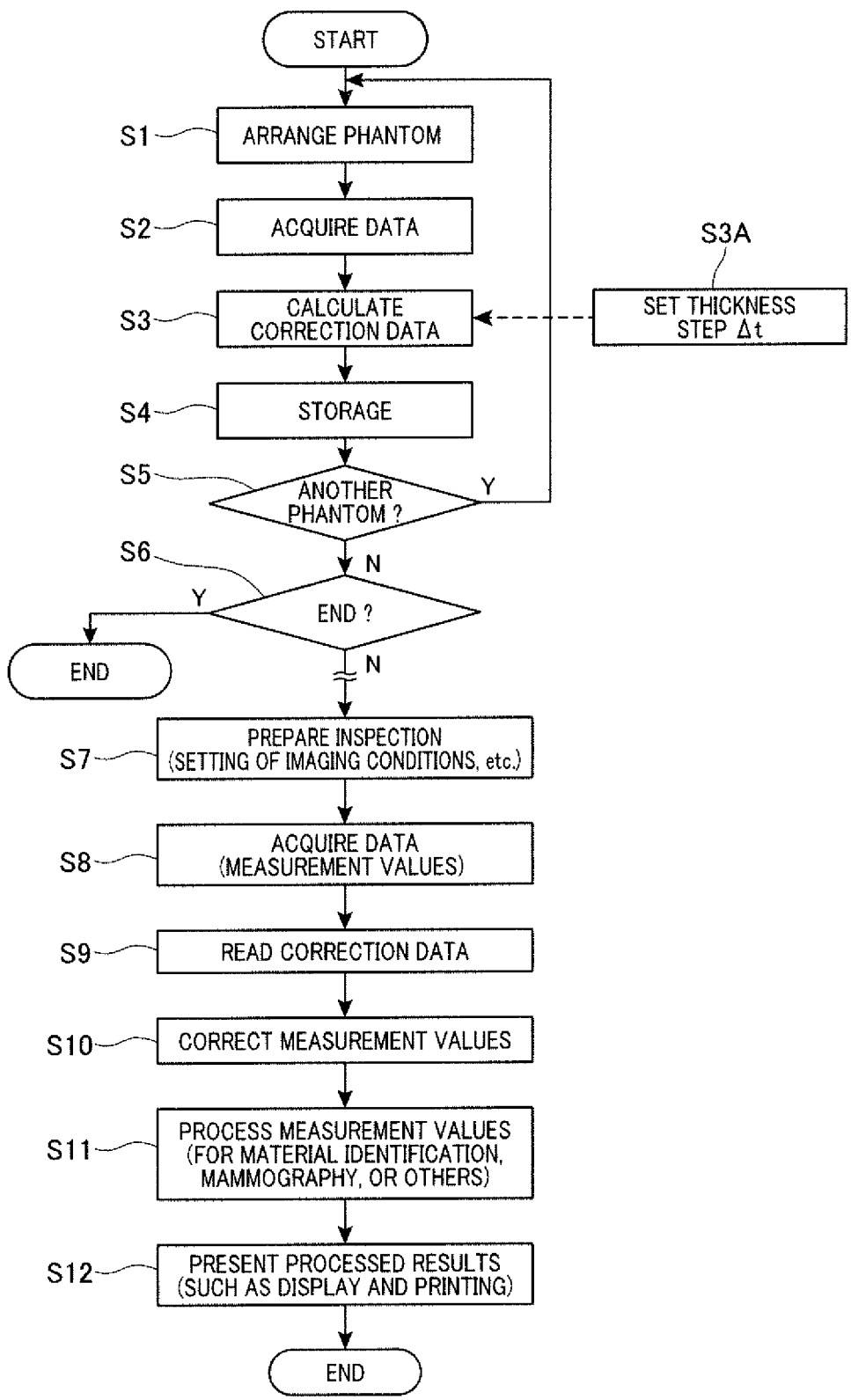
FIG. 10 is a flowchart exemplifying an outline of processes from acquisition of correcting data, and correction and usage of measured data (the flowchart also explaining a first variation)

The processor 35 of the data processing apparatus 12 performs a process exemplified in FIG. 10. The processor 35 instructs an operator to arrange a desired substance phantom FM1 (FM2) at a determined inspection position in the X-ray apparatus 10 (step S1), After this arrangement, the X-ray apparatus 10 is driven to scan the phantom FM1 with X-rays in order to acquire counted values for the phantom (step S2). The processor 35 then calculates correcting data CA) (step S3), and store in the first data storage area 33B of the ROM 33 for preservation (step S4).

Then the processor 35 confirms whether or not another phantom is to be subjected to the similar calculation, interactively with the operator (step S5). If another phantom is desired for generating the correcting data, the processing returns to step S1 to repeat the foregoing process with the next phantom FM2 (FM1). The number of phantoms are not limited to two, but many other phantoms are usable depending on types or properties of objects being inspected or foreign matter. For each phantom, the correcting data are prepared. When this series of the previous measurement and correcting data calculation for the phantoms are desired to end, the processing is also ended (step S6, YES). In contrast, the processing will not be ended (step S6, NO), the process for the inspection is performed at and after step S7.

First, the processor 35 performs, interactively with the operator, preparation work for the inspection, which includes selection of an object being examined and setting of imaging conditions (step S7). Then the processor 35 drives the X-ray apparatus 10 to an X-ray scan (for example, a foreign matter inspection: step S8). By this scan, frame data of the object, i.e., measured values are acquired, for example, at the respective pixels Pin each of the X-ray energy bins, $Bin_1$ (for example, i=1, 2, 3).

The processor 35 then reads the correcting data $C_i(t)$ of the object (for example, a food item (e.g., peppers)), which have been stored in the first data storage area 33B of the ROM 33 (step S9). The processor 35 calculates linear attenuation values $\mu_o*t$ corresponding to the monochromatic X-rays, by multiplying, by the correcting data $C_i(t)$, the imaginary attenuation values pot obtained from the measured values (step S10). This results in correcting the imaginary attenuation values $\mu_i m(t)*t$, which are along a curved characteristic without being along a linear characteristic. This can be regarded as a comprehensive calibration which was performed after the actual measurement, as if error factors, which cannot be understood without actual X-ray detection, have been understood even before the actual X-ray detection. This correction (i.e., calibration) can be performed at every pixel area PA.

After this, the processor 35 process the measured values interactively with the operator to check whether or not foreign matter which may be contained in the object, identify the type of foreign matter, and/or carry out other necessary processes (step S11). When identifying foreign matter, the correcting data $C_i(t)$ generated by using phantoms made of aluminum and/or other substances are used in the same manner as described.

This identification technique is known, for example, by patent publications of JP-A 2013419000 and WO 2014 181889(A1). The present inventors have proposed improvements of such identification technique by patent publications of JP application numbers 2015-023446 and 2015-85551.

Further, the processor 35 presents processed results of the measured values via, for example, various display and printing modes (step S12), before ending the process.

In the foregoing processing, the steps S1 and S2 functionally configure the foregoing characteristic acquisition unit 51 (serving as characteristic acquiring means), the steps S3 and S4 functionally configure the foregoing correction data calculation unit 52 (serving as correcting data calculation means), the steps S9 and S10 functionally configure the foregoing correcting unit 53 (serving as correcting means). Moreover, the step S11 functionally corresponds to processing mans and step S12 functionally corresponds to presenting means.

As examples of presentation of the processed results, exemplified are presenting a three-dimensional scatter diagram and an absorption vector length image.

Figure 11:
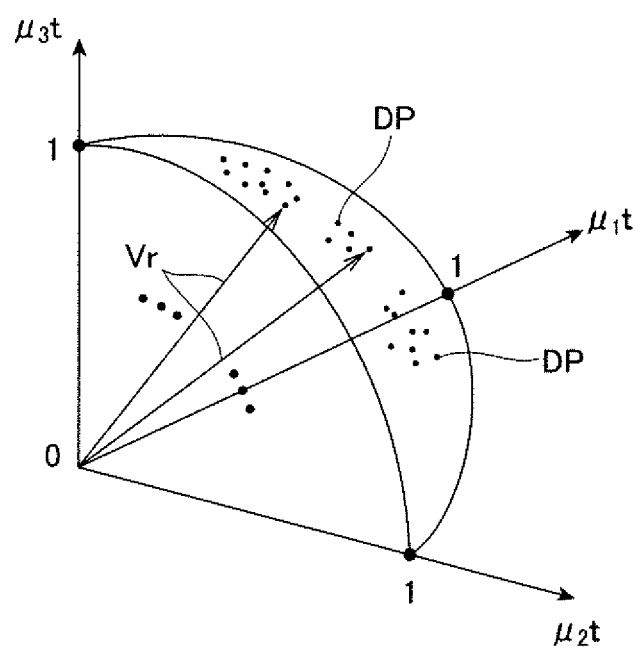
FIG. 11 is an illustration pictorially explaining a concept of a three-dimensional scatter diagram.
Figure 12:
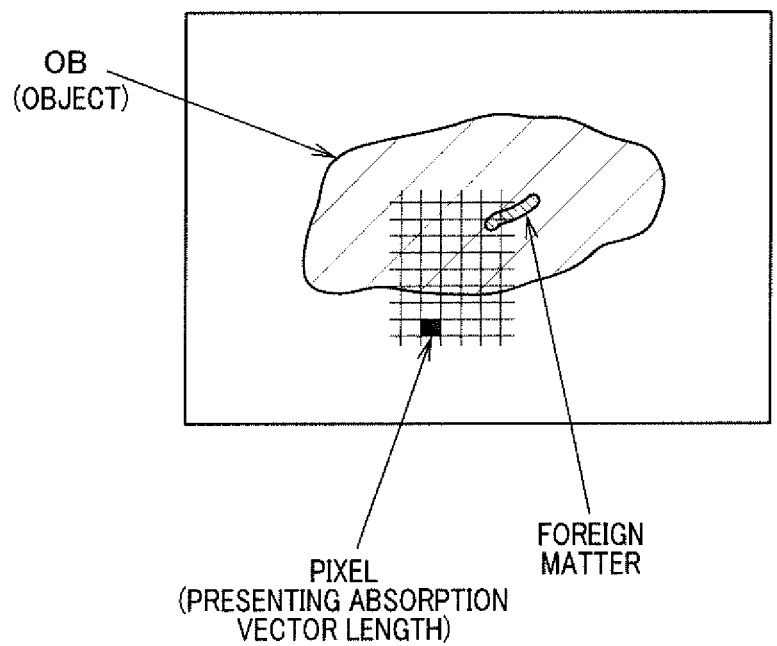
FIG. 12 is an illustration pictorially explaining a concept of an absorption vector length image.

In the present embodiment, the linear attenuation amounts $\mu_i t$ have three degrees of freedom, because of use of three X-ray energy bins, $Bin_i$. Hence, a three-dimensional vector ($\mu_1 t$, $\mu_2 t$, $\mu_3 t$) can be set at each pixel, and from this, a three-dimensional linear attenuation vector ($\mu_1$, $\mu_2$, $\mu_3$) can be obtained. A length of this vector ($\mu_1$, $\mu_2$, $\mu_3$) that is, a linear attenuation vector length, $(\mu_1^2+\mu_2^2+\mu_3^2)^{1/2}$ can be used as a denominator in calculating a normalized three-dimensional vector (herein referred to as a linear attenuation vector) from a formula of:

$$(\mu_1, \mu_2, \mu_3)/(\mu_1^2+\mu_2^2+\mu_3^2)^{1/2},$$

where the factor of the thickness t disappears from this linear attenuation vector. When a three-dimensional Cartesian coordinate system whose three axes are $\mu_1 t$, $\mu_2 t$, and $\mu_3 t$ is set, the three-dimensional linear attenuation vector has a start point at the origin of the three-dimensional coordinate system and an end point on a spherical surface, of which radius is 1. This three-dimensional linear attenuation vector is calculated as each pixel and mapped in the three-dimensional coordinate system, resulting in that the end points are mapped within a certain area around a point mapped on the spherical surface. This area is composed of an aggregation of scattered points mapped with statistical errors. The inventors refer to this three-dimensional scatter-point map as a three-dimensional scatter diagram, which is exemplified in FIG. 11. In FIG. 11, a reference symbol Vr indicates a three-dimensional linear attenuation vector and a reference symbol DP indicates a scattered point.

How the end points (scatter points) of the linear attenuation vectors are mapped on the spherical surface, that is, in the three-dimensional scatter diagram, is inherent to the type itself of a substance contained in an object. In other words, the substance type is changed, the scatter points are also changed, which is true from a theoretical view point. These changes are led to identification of types of substances (materials). This was confirmed by a simulation carried out by the inventors.

Moreover, the vector length at each pixel can be calculated by a formula of $t(\mu_1^2+\mu_2^2+\mu_3^2)^{1/2}$.

The inventors refer to this scalar value as an absorption vector length (or a pseudo-absorption value). This absorption vector length can be formed as a two-dimensional image whose pixels are indicated by the absorption vector length. The inventors refer this two-dimensional image as an absorption vector length image (or a pseudo-absorption image), which is exemplified in FIG. 12.

By way of another example, either the three-dimensional scatter diagram or the absorption vector length image can be calculated.

Simulations conducted by the inventors showed that the foregoing correction (or calibration) of error factors, such as beam hardening, which influence an X-ray spectrum, raises a depiction performance of a substance depicted in the three-dimensional scatter diagram, and the absorption vector length image shows proportions to thicknesses of a substance.

In this way, according to the X-ray apparatus of the present embodiment, the detector is used which is capable of counting X-ray photons in each of a plurality of X-ray energy bins. Using this detector, an object is scanned with X-rays having a continuous energy spectrum. Errors of measured values can be reduced greatly, even though the measured values may contain error factors such as X-ray attenuated factors including beam hardening and heeling effect and circuitry factors such as charge sharing. It is thus possible to correct the measured values (counts) as if the measured values have been calibrated before the processing, thus raising reliably. When performing an image reconstruction or an analysis based on such measured values, the processes are more stable, thus being more reliable. When identifying the types or properties of substances based on the measured values, the identification can be conducted with higher precision.

Moreover, conventionally, even if in one X-ray energy bin and for the same substance, an effective energy raises with an increase in the substance thickness due to the beam hardening. Because of this influence, it is difficult to obtain a characteristic obtained by assigning a representative of monochromatic X-rays to a single X-ray energy bin. However, in the present embodiment, this difficulty can be overcome as if designated monochromatic X-rays are radiated in each of the X-ray energy bins so that X-ray photons virtually behave on the radiated monochromatic X-rays, and measured values in each of the X-ray energy bins are corrected accordingly. It is thus possible to reduce error factors in the counts due to the beam hardening and others, and reduce distortions, noise and other factors in inspection images and analyzed maps, thereby providing inspected information with higher reliability.

Depending on a composition of substances of an object being inspected, it is not always necessary to prepare for a plurality of sets of correcting data, but it is sometimes sufficient if a set of correcting data is prepared using a material similar in X-ray transmission characteristics to the main substance of an object. In this case, it may be possible to use such correcting data to apply material identification to other components of the object, with precision. For instance, in the mammography, there can be seen a composition of mammary grand, fat, malignancy, calcification, and others, it is sufficient to prepare correcting data using a material whose effective atomic number is similar to that of average elements such as mammary gland which is normal tissue and fat, which makes it possible to realized highly accurate material identification.

In addition, this correction method can also be applied to a system detecting X-rays transmitted through an object by using an X-ray detector (or X-ray sensor) provided with a single pixel or an X-ray spectrometer. Even if in such a system, provided that information about the photon counts is acquired statistically fully and with precision, it is definitely possible to perform meaningful material identification.

From another point of view, it is possible to apply the configuration of the present invention to detection of the weight and/or thickness of substances. Namely, this results from the foregoing embodiment in which the correction is performed to be according to a linear line about both X-ray attenuation values and substance thicknesses in which the line passes through the origin of the coordinate system. Accordingly, if an object is composed of main substances whose kinds are the same and the linear attenuation coefficients of the substances are known, the weights and thicknesses of the restive substances can be calculated accurately. As to X-ray weight measurement of objects, such measurement has already been realized in some X-ray in-line inspection apparatuses used in the food foreign-matter inspection. However, this measurement has been realized in only inspections directed to a simple composition of materials, such as vegetables, which are absolutely limited in their application ranges (such as thickness or object types). The photon counting detector has a wider dynamic range, the range of applications to which higher-accurate weight measurement is applicable can be spread greatly, as long as X-ray radiation conditions are adjusted so as not to make it zero counts in each X-ray energy bin. In addition, it is supposed that, unlike the present invention, it is difficult to easily estimate the thickness of an object by using the conventional techniques.

MODIFICATIONS

The foregoing embodiment has been explained about how to acquire the correcting data, and this technique can still develop in various modified modes.

First Modification

First of all, the linear target characteristic explained with FIG. 7 can be modified in various modes. The foregoing target characteristic is just one example. How to generate the target characteristic, which has been stated, is also just one example and can be designed in another way.

For instance, a linear line can be set as a target characteristic which connects, as shown in FIG. 7, the origin of the coordinate system and an intersection point where a representative thickness $t_r$ of an object and an X-ray attenuation amount $\mu t_r$ corresponding to the representative thickness $t_r$. Such a representative thickness $t_r$ can be set by referring to a plurality of mutually different thicknesses t of a substance which is similar in type or which can be approximated in X-ray transmission properties to an object being examined. This target characteristic can be calculated by the processor 35 or an external processing device in advance, and data of the target characteristic can be stored in the first data storage area 33B of the ROM 33. At step S3 shown in FIG. 10 described, the data of such target characteristic is read from the first data storage area 33B of the ROM 33, and can be used for calculating the correcting data.

Second Modification

A second medication also relates to another way of setting the target characteristic.

This setting technique is to set a linear line serving as a target characteristic, which has a designated gradient and which passes the origin of the coordinate system. The gradient is set to be a linear attenuation coefficient calculated based on a theoretical value for an effective or fixed energy in each of the X-ray energy bins.

Figure 13:
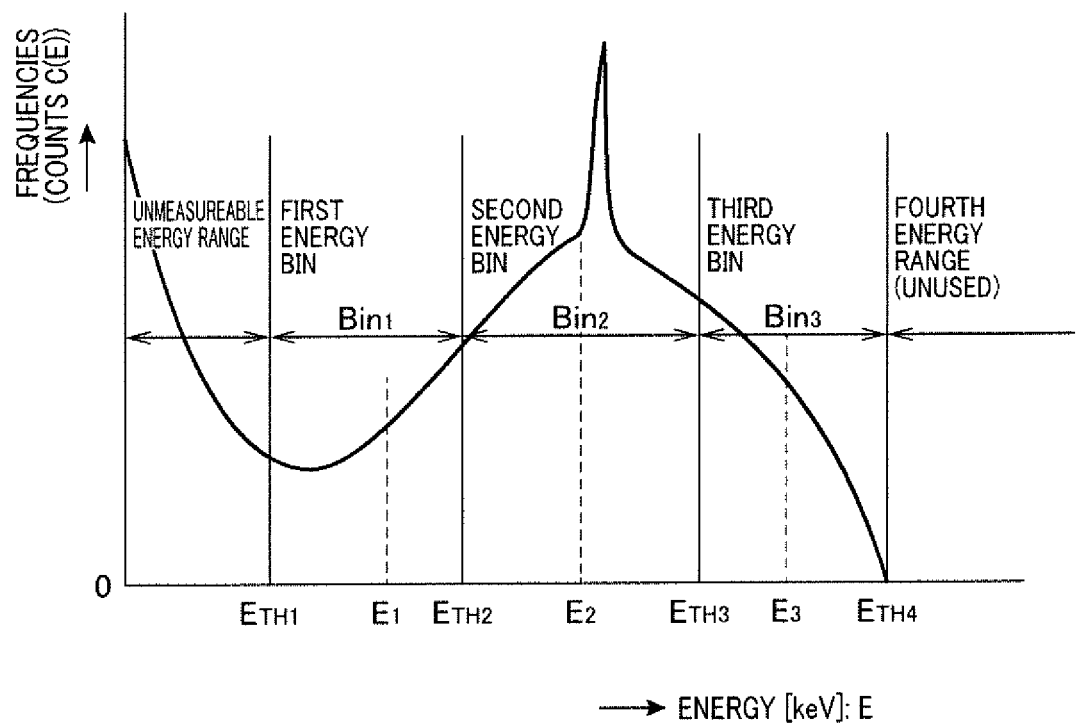
FIG. 13 is a graph showing an X-ray energy spectrum according a second modification.

A case which uses an effective energy in each of the X-ray energy bins will now be described. FIG. 13 pictorially exemplifies an X-ray energy spectrum. In this spectrum, similarly to that shown in FIG. 3, the three energy bins, $Bin_1$ to $Bin_3$, are set, in which an effective energy amount $E_i$ in the respective energy bins, $Bin_1$ to $Bin_3$, can be calculated based on the following formula:

$$\int_{E_{THi}}^{E_i} C(E)dE = \frac{1}{2} \int_{E_{THi+1}}^{E_{i+1}} C(E)dE,$$

where i=1, 2 and 3.

This calculation shows that a count of X-ray photons counted between an energy threshold $E_{TH_i}$ to an effective energy $E_i$ is equal to ½ of a count of X-ray photons counted between the effective energy $E_i$ and an effective energy $E_{TH_{i+1}}$.

Figure 14:
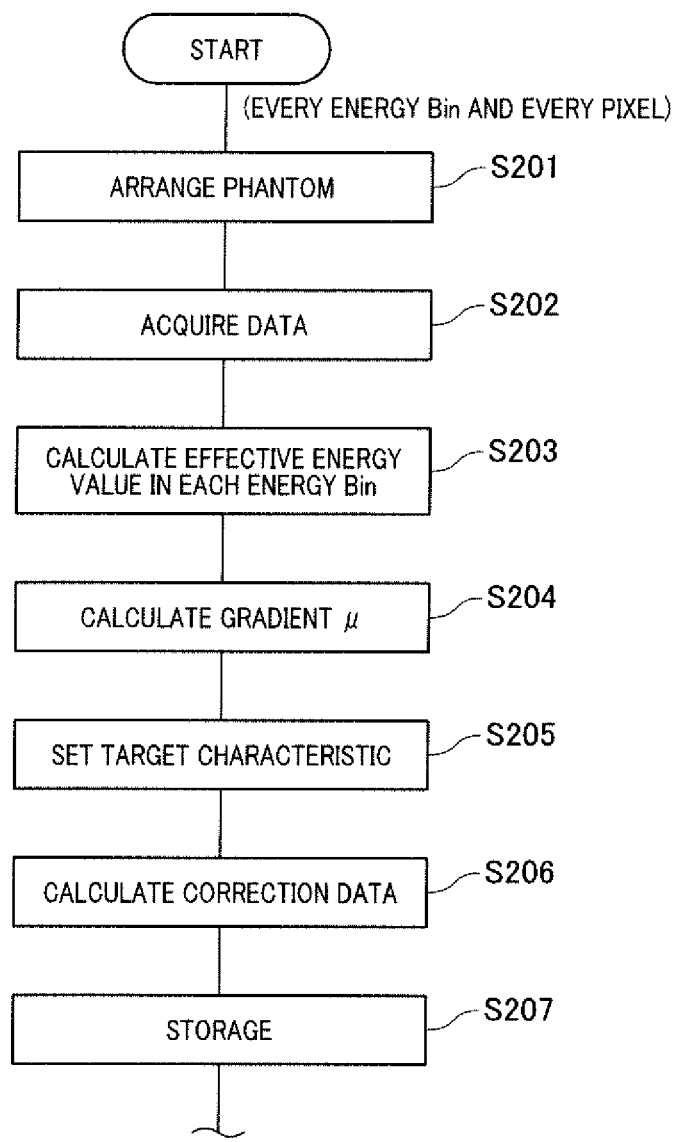
FIG. 14 is a partial flowchart explaining a part of processes performed by a processor, according to the second modification.

In consideration of this fact, a process substantially shown in FIG. 14 is carried out. Specifically, similarly to the foregoing embodiment, in an X-ray energy spectrum of a substance (phantom) imitating an object in view of the linear attenuation coefficients (refer to steps S201 and S202 in FIG. 14), effective energy amounts $E_i$ are calculated based on the foregoing formula (step S203). Values λ (linear attenuation coefficients) each are obtained by multiplying, by a density σ, mass attenuation coefficients (μ/σ: μ is a linear attenuation coefficient; and a is a density) at the respective effective X-ray energies $E_i$. And, the values p are employed as gradients in the respective X-ray bins (step S204). The processor 35 then sets, as a target characteristic in each X-ray energy bin, a linear line having a calculated gradient and passing the origin O of the coordinate system, and, based don this target characteristic, calculate correcting data (i.e., calibration data) in each X-ray energy bin (steps S205 and S206). In addition, the calculated correcting data are stored in the first data storage area 33B of the ROM 33 (step S207).

As a result, in the similar way to that shown in FIG. 7, the target characteristic is set at every pixel or at every pixel area composed of a given number of pixels in each of the X-ray energy bins, and the correcting data is produced therefor. This calculation is followed by the process described by step S5 and thereafter in FIG. 10, thereby setting more accurate target characteristics with lesser amounts of calculation, thereby allowing the beam hardening correction in an easier manner.

Alternatively, instead of using the effective energy in each of the X-ray energy bins, a fixed energy value, such as a center of a range defined by the width of each of the energy bins can be adopted to set the target characteristics.

Third Modification

Figure 15:
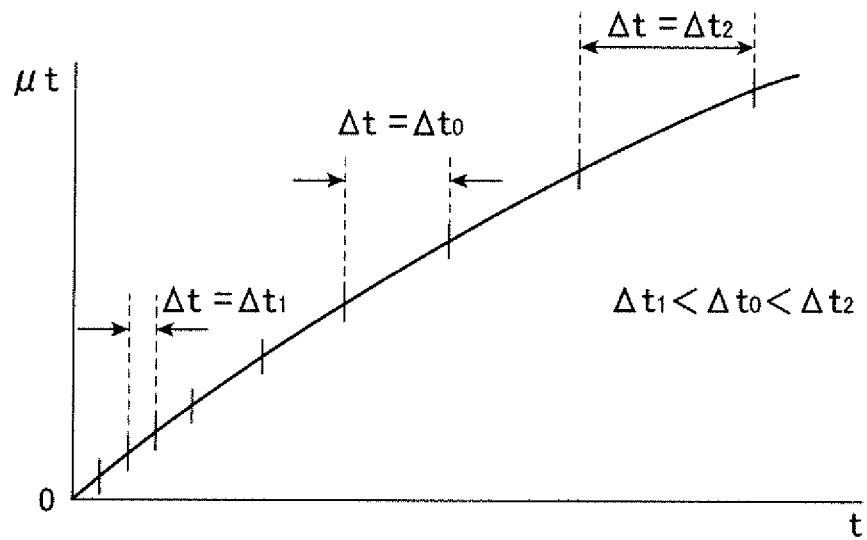
FIG. 15 is a graph explaining an X-ray energy spectrum according to a third modification.

A third embodiment relates to a technique for changing a thickness step Δt for acquiring the correcting data, depending on largeness of the thicknesses t provided by a calibration phantom. The reason for this modification is that it is generally required to carry out the beam hardening correction with higher accuracy as the thickness t becomes thinner. Hence, as pictorially shown in FIG. 15, the thinner the thickness t of a calibration phantom, the smaller the thickness step Δt (for example, Δt1<Δt2). Changing and setting the thickness step Δt can be carried out by the processor 35 at step S3 shown in FIG. 10 (refer to step S3A). By this, depending on the thicknesses t, the correcting data (multiplication-correcting coefficients $C_i(t)$: i.e., calibration data) can be obtained at every thickness step which is set more finely.

Fourth Modification

Figure 16:
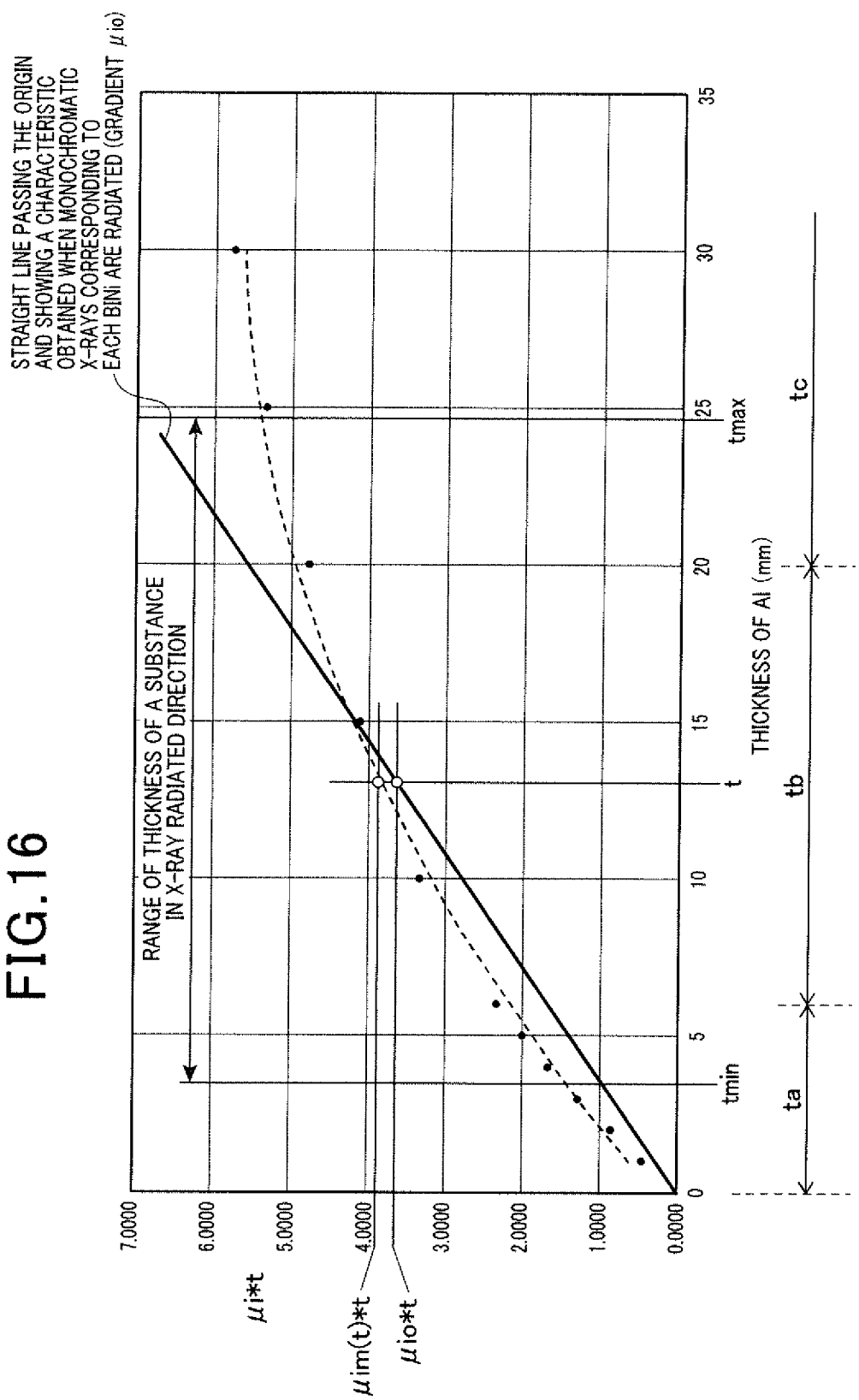
FIG. 16 is a graph explain how to generate correcting data for correcting influence of the beam hardening and other factors, which explains a fourth modification.

In the foregoing embodiment, as shown in FIG. 7, a whole range of the thicknesses t supposedly in size assigned a substance (object) is handled as one thickens section, the characteristic of X-ray attenuation amounts μt is approximated by the quadratic function or other functions, and the correcting data is acquired which is for correcting a curve approximated formula to a target characteristic having a gradient $μ_{i0}$. This acquisition can be developed into various other forms. For example, as shown in FIG. 16, the range of thicknesses of an object can be divided into a plurality of sections including for example thinner sections ta, intermediate sections tb, and thicker sections tc. Every section, the foregoing approximation and correcting data generation can be performed.

For such a purpose, at step S3 in FIG. 10, the processor 35 approximates, to functions, X-ray attenuation amounts μt measured using a phantom, for every section ta (tb, tc) (step S31). Then the processor 35 calculates correcting data to correct (or fit) curves shown by the approximation formulae to target characteristics having gradients $μ_{io}$, for the respective sections ta, tb and tc (step S32). Finally, the processor 35 connects the correcting data in the respective sections into a single set of correcting data, which are then stored in the first data storage area 33B of the ROM 33 (step S33).

As an alternative example, of the three sections ta, tb and tc, any or two sections can be selected as priority correcting section(s), which is then subjected to the foregoing processing.

In this way, the whole range of thicknesses t of an object or a part thereof is given the correcting data with finer ranges.

Fifth Modification

A fifth modification is similar to the second modification in dividing the thicknesses into sub ranges, but different from that in that dividing the sections and calculating correcting data are carried out with shifting in the direction indicating the thicknesses t in the coordinate system.

Figure 18:
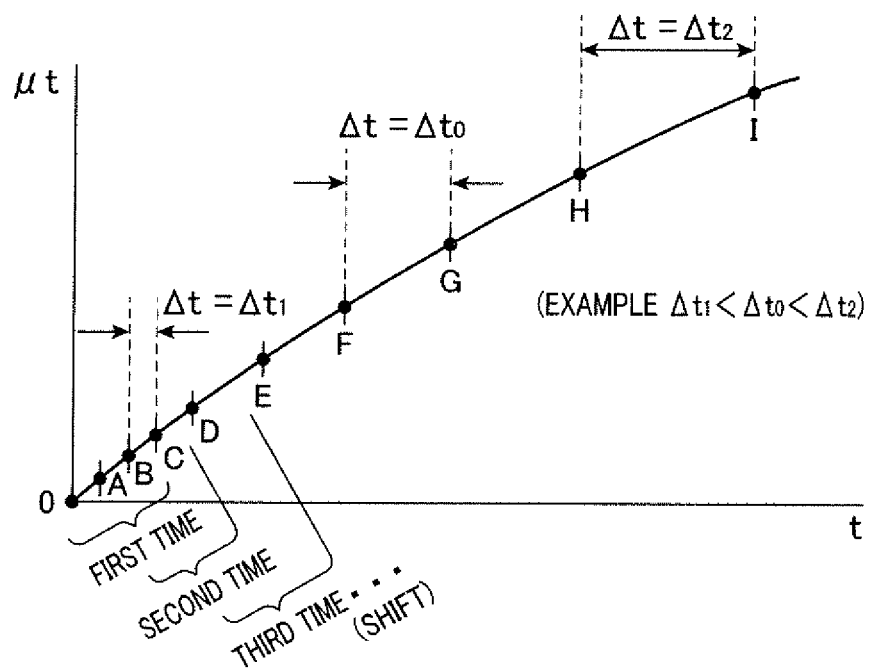
FIG. 18 is a graph of an X-ray energy spectrum explaining how to designate calculation points, which is according to a fifth modification.

Referring to FIG. 18, a technique of the fifth modification will now be described conceptually. A curve shown in FIG. 18 conceptually shows the curve of imaginary attenuation values $μ_r m(t)*t$, which is measured by using the calibration phantom, which is described with FIG. 16. Firstly, a curve portion passing, for example, three points O (the origin), A and B is approximated by for example a quadratic curve. As to a thickness step Δt spaced between the first two points O and A among the three points O, A and B, or a thickness step Δt provided by more finely dividing the range spaced between the two points O and A, correcting data is first produced. In this case, the thickness step Δt may be variable or fixed in the thickness direction. As the next process, the calculation points are shifted to a thicker side in the thickness t direction, so that a curve portion passing new three points A, B and C is subjected to approximation using for example a quadratic function, and then subjected to generation of correcting data at a thickness step Δt derived from the first two points A and B or provided by more finely dividing the space between the two points A and B. then the calculation points are shifted further towards the thicker side in the thicknesses t, which allows the new three points B, C and D to be processed in the same manner. At the fourth cycle and thereafter, the same process as the above is performed repeatedly. In this method, it is possible to widen or fix the width of a section assigned to the calculation points A, B, C, D, . . . , as the thickness t becomes thicker in the thickness direction. Even in the fixed width of the section, the thickness step Δt can be set to be larger with increase in the thickness t.

In this modification, the processor 35 performs a process shown in FIG. 19 as a part of the processing at the foregoing steps S3 and S4. Based on preset information, the processor 35 sets a plurality of calculation points O, A, B, C, D, . . . including the origin O (step S310). The processor 35 then designates the first set of three points O, A and B including the origin O (step S311), and calculates or stores correcting data at a thickness step Δt provided between the two points O and A or at more finely divided widths between the two points O and A (step S312). Further, the calculation points are shifted, for example, by one point towards a thickness-larger side to designate the next three points A, B and C (step S313). In the same way as the above, correcting data are calculated and stored at the thickness step Δt provided between the two points A and B or at more finely divided widths between the two points A and B (step S313). This process is repeated until all the calculation points are completed from being subjected to the calculation (step S315). After this, the processor 35 reads the correcting data for each section and connects them smoothly by using a smoothing process (step S316). Such connected correcting data is again stored in the first data storage area 33B of the ROM 33 (step S317). The processing then proceeds, for instance, to step S5 and thereafter in FIG. 10 described.

In this way, with the calculation points shifted, the correcting data are calculated, thus enabling acquisition of the correcting data in a finer manner as described.

Figure 17:
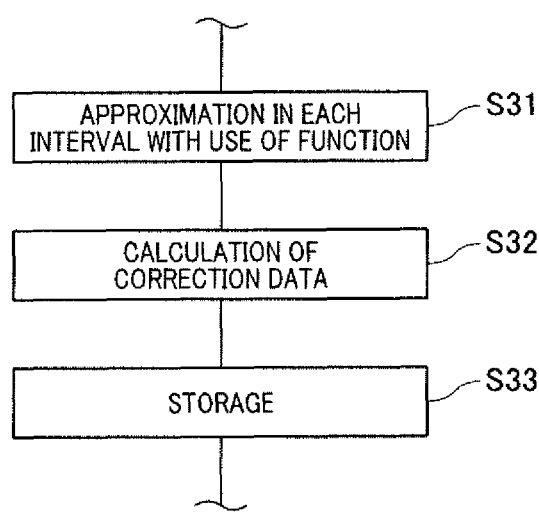
FIG. 17 is a partial flowchart explaining a part of processes performed by the processor, according to the fourth modification.

In the forgoing various modifications, as to FIG. 14, step S202 functionally provides characteristic acquiring means, steps S203 to S205 functionally provide correcting data calculating means, and step S207 functionally configures part of the storage means. As to FIG. 17, steps S31 and S32 functionally configure part of correcting data calculating means, and step S33 functionally configures the storage means. As to FIG. 19, steps S310 to S317 functionally configure part of correcting data calculating means. Of these, step S318 corresponds to part of the storage means.

The present invention will not be limited to the configurations stated in the foregoing embodiment and modifications, but may be practiced with various known embodiments within a gist of the present invention.

REFERENCE SIGNS LIST

10 X-ray apparatus
21 X-ray tube
24 detector
25 data acquisition circuit
12 data processing apparatus (computer)
33 ROM
33A program storage area
33B first data storage area (also corresponding to part of reference data storage means)
33C second data storage area
35 processor (configuring main part of processing means: CPU mounted)
37 input device
38 display unit (corresponding to part of presenting means)
51 characteristic acquisition unit (corresponding to characteristic acquiring means)
52 correction data calculation unit (corresponding to correcting data calculating means)
53 correcting unit (corresponding to correcting means)
P pixel
PA pixel area
OB object
FM1, FM2 phantom

What is claimed is:

1. An X-ray apparatus which inspects an object, wherein beam-shaped X-rays having a preset continuous X-ray spectrum are radiated to an object and the object is inspected with the X-rays transmitted through the object, the apparatus comprising:
a photon counting detector outputting a count by detecting the X-rays transmitted through a substance and measuring a count of number of photons of the X-rays in each of one or more X-ray energy bins which are set in advance, the substance being the same in type as the object or consisting of materials which are regarded as being similar in an effective atomic number to the object;
characteristic acquiring means for acquiring a characteristic showing X-ray attenuation amounts μt based on the count outputted from the detector in each of the X-ray energy bins, the X-ray attenuation amounts μt being defined by mutually different known thicknesses t of the object in a transmission direction of X-ray fluxes of the X-rays and linear attenuation coefficients μ of the object; and
correcting data calculating means for calculating, for each of the X-ray energy bins, correcting data, the correcting data replacing a characteristic of the X-ray attenuation amounts μt acquired by the characteristic acquiring means, with a linear target characteristic passing an origin of a two-dimensional coordinate system, the coordinate system having two axes which are mutually perpendicular, one of the axes being given to the thicknesses t and the other of the axes being given to the X-ray attenuation amounts μt.

2. The X-ray apparatus of claim 1, wherein
the detector is provided with a plurality of pixels receiving incidence of the X-rays and is configured to detect the X-rays transmitted through the object at the respective pixels and count the number of X-ray photons at the respective pixels and in the respective one or more X-ray energy bins to output the count,
the characteristic acquiring means is configured to acquire, based on the count outputted from the detector, the characteristic showing the X-ray attenuation amounts μt in the respective X-ray energy bins and at the respective pixels or at respective pixel areas each consisting of two or more pixels, and the correcting data calculating means is configured to calculate the correcting data in the respective X-ray energy bins and at the respective pixels or at the respective pixel areas.

3. The X-ray apparatus of claim 1, wherein the apparatus comprises correcting means for correcting the count based on the correcting data in the respective X-ray energy bins and at the respective pixels or at the respective pixel areas.

4. The X-ray apparatus of claim 3, wherein the apparatus comprises processing means for processing data for the inspection of the object based on the count corrected by the correcting means.

5. The X-ray apparatus of claim 4,
wherein the processing means is configured to calculate, at each of the pixels, vector information in relation to the X-ray attenuation of the object based on the data corrected by the correcting means; and
the X-ray apparatus comprises presenting means having a display unit, the presenting means being configured to present the vector information on the display unit,
wherein the processing means is configured to calculate, as the vector information, n-dimensional normalized linear attenuation vectors defined by a formula of:

$$(\mu_1, \mu_2, \ldots, \mu_n)/(\mu_1^2 + \mu_2^2 + \mu_n^2)^{1/2},$$

where the X-ray energy bins are composed of n bins (n is a 2 or more positive integer) and $\mu_i$(i=1 to n) are imaginary average linear attenuation coefficients, t is a thickness of the object in a projected direction of the X-rays, and ($\mu_1 t, \mu_2 t, \ldots, \mu_n t$) are n-dimensional vectors defined by the imaginary average linear attenuation coefficients $\mu_i$(i=1, 2, ..., n) and the thicknesses t.

6. The X-ray apparatus of claim 4,
wherein the processing means is configured to calculate, at each of the pixels, an absorption vector length in relation to the X-ray attenuation of the object based on the data corrected by the correcting means; and
the X-ray apparatus comprises presenting means having a display unit, the presenting means being configured to present the absorption vector length on the display unit,
wherein the processing means is configured to calculate, as the absorption vector length, a vector length defined by a formula of:

$$t \times (\mu_1^2 + \mu_2^2 + \ldots + \mu_n^2)^{1/2},$$

where the X-ray energy bins are composed of n bins (n is a 2 or more positive integer) and $\mu_i$(i=1, 2, ..., n) are imaginary average linear attenuation coefficients, t is a thickness of the object in a projected direction of the X-rays, and ($\mu_1 t, \mu_2 t, \ldots, \mu_n t$) are n-dimensional vectors defined by the imaginary average linear attenuation coefficients $\mu_i$(i=1, 2, ..., n) and the thicknesses t.

7. The X-ray apparatus of claim 4, wherein
the processing means is configured to identify at least one of i) a type or a property of either the object or a substance composing a part of the object, ii) whether or not foreign matter is attached to an outside of the object or mixed inside the object, iii) a type or a property of the foreign matter, iv) a weight of foreign matter which may be included in the object or a substance composing a part of the object, and v) a thickness of foreign matter which may be included in the object or a substance composing a part of the object.

8. The X-ray apparatus of claim 3, comprising a phantom made of a substance which is the same in type as the object or a substance composed of a material of which attenuation coefficient to the X-rays is regarded as being substantially similar to the object, the phantom having a plurality of known thicknesses in a transmitted direction of the X-rays in an actual measurement,
wherein the characteristic acquiring means is configured to acquire the count from the detector under the radiation of the X-rays in a state where the phantom is arranged at a positon where the object is actually located during the inspection, and to calculate the characteristic of the X-ray attenuation amounts μt of the phantom in a direction along which fluxes of the X-rays are transmitted, based on the count,
the correcting data calculating means comprises reference data storing means storing reference data therein, the reference data being calculated as the correcting data for correcting the characteristic of the X-ray attenuation amounts μt to the linear target characteristic, from the characteristic of the X-ray attenuation amounts μt acquired by the characteristic acquiring means, and
the correcting means is configured to correct the count during the inspection with reference to the correcting data stored in the reference data storing means.

9. The X-ray apparatus of claim 1 wherein the correcting data calculating means comprises
approximating means for approximating, with a function of the thicknesses t, the characteristic of the X-ray attenuation amounts acquired by the characteristic acquiring means, and
correction-coefficient calculating means for calculating, as the correcting data, correction coefficients for replacing the characteristic of the X-ray attenuation amounts μt approximated with the function with the linear target characteristic of the X-ray attenuation amounts μt corresponding to monochromatic X-rays having an X-ray energy representing the X-ray energy bins.

10. The X-ray apparatus of claim 9, wherein
the approximating means is configured to approximate the characteristic of the X-ray attenuation amounts μt with the function of the thicknesses t in each of a plurality of sections provided by dividing the one axis assigned to the thicknesses t, and
the correction-coefficient calculating means is configured to calculate the correction coefficients in each of the sections.

11. The X-ray apparatus of claim 10, wherein
the approximating means is configured to sequentially approximate, with the function of the thicknesses t, the characteristic of the X-ray attenuation amounts μt dedicated to a set of a predetermined number of points on the one axis assigned to the thicknesses t, with the set of the points shifted repeatedly, and
the correction-coefficient calculating means is configured to calculate the correction coefficients in each of the sets of the predetermined number of points subjected to the approximation.

12. The X-ray apparatus of claim 11, wherein the correction-coefficient calculating means is configured to repeatedly calculate the correction coefficients in a range of the thicknesses t, the range being provided by points belonging to a part of the plurality of points and continued from the range which was set last time.

13. The X-ray apparatus of claim 10, wherein the function of the thicknesses t is a quadratic function of the thicknesses t.

14. The X-ray apparatus of claim 9, wherein the apparatus comprises storage means storing therein the correcting data calculated by the correction-coefficient calculating means and information indicative of the function approximated by the approximating means.

15. The X-ray apparatus of claim 1, wherein the X-ray energy bins are two or more in number ($Bin_i$: i=1, 2, ...).

16. The X-ray apparatus of claim 1, wherein the correcting data calculating means comprises target characteristic setting means for setting, as the linear target characteristic, a linear line connecting an intersection and the origin, the intersection being provided by a representative thickness tr given to the object and the X-ray attenuation amount μt corresponding to the representative thickness tr, the representative thickness being set based on the plurality of mutually different thicknesses of a substance which is the same or similar in type as or to the object.

17. The X-ray apparatus of claim 1, comprising target characteristic setting means for setting, as the linear target characteristic, a linear line passing the origin and having a gradient corresponding to a linear attenuation coefficient calculated based on an X-ray effective energy or a theoretical value of a fixed X-ray energy in each of the X-ray energy bins.

18. A data processing apparatus installed in an X-ray apparatus which inspects an object, wherein beam-shaped X-rays having a preset continuous X-ray spectrum are radiated to an object, the X-rays transmitted through the object are detected to measure a count of photons of the X-rays in each of previously set one or more energy bins, the data processing apparatus comprising:
    characteristic acquiring means for acquiring a characteristic showing X-ray attenuation amounts μt based on the outputted count in each of the X-ray energy bins, the X-ray attenuation amounts μt being defined by mutually different known thicknesses t of the object in a transmission direction of X-ray fluxes of the X-rays and linear attenuation coefficients μ of the object; and
    correcting data calculating means for calculating, for each of the X-ray energy bins, correcting data, the correcting data replacing a characteristic of the X-ray attenuation amounts μt acquired by the characteristic acquiring means, with a linear target characteristic passing an origin of a two-dimensional coordinate system, the coordinate system having two axes which are mutually perpendicular, one of the axes being given to the thicknesses t and the other of the axes being given to the X-ray attenuation amounts μt.

19. A data processing method performed in an X-ray apparatus which inspects an object, wherein beam-shaped X-rays having a preset continuous X-ray spectrum are radiated to an object, the X-rays transmitted through the object are detected to measure a count of photons of the X-rays in each of previously set one or more energy bins, the data processing method comprising steps of:
    acquiring a characteristic showing X-ray attenuation amounts μt based on the outputted count in each of the X-ray energy bins, the X-ray attenuation amounts μt being defined by mutually different known thicknesses t of the object in a transmission direction of X-ray fluxes of the X-rays and linear attenuation coefficients μ of the object; and
    correcting data calculating means for calculating, for each of the X-ray energy bins, correcting data, the correcting data replacing a characteristic of the acquired X-ray attenuation amounts μt, with a linear target characteristic passing an origin of a two-dimensional coordinate system, the coordinate system having two axes which are mutually perpendicular, one of the axes being given to the thicknesses t and the other of the axes being given to the X-ray attenuation amounts μt.

20. The data processing method of claim 19, wherein the substance is a phantom imitating the object in terms of the linear attenuation coefficients, and
    the material has an effective atomic number belonging to a range of ±5 of an effective atomic number of the object.

21. A data processing apparatus installed in an X-ray apparatus which inspects an object, wherein beam-shaped X-rays having a continuous X-ray spectrum are radiated to an object, the X-rays transmitted through the object are detected to measure a count of photons of the X-rays in each of previously set two or more energy bins, the data processing apparatus comprising:
    an interface; and
    a processor configured to receive, via the interface, information showing the count of photons of the X-rays,
    acquire, based on the received information, a characteristic showing X-ray attenuation amounts μt based on the outputted count in i) each of the X-ray energy bins and ii) each of at pixels or pixel areas each consisting of two or more of the pixels, the pixels being provided at a detector detecting the X-rays transmitted through the object, the X-ray attenuation amounts μt being defined by mutually different known thicknesses t of the object in a transmission direction of X-ray fluxes of the X-rays and linear attenuation coefficients μ of the object;
    calculate, for each of the X-ray energy bins and for each of the pixels or the pixel areas, correcting data, the correcting data replacing a characteristic of the X-acquired ray attenuation amounts μt, with a linear target characteristic passing an origin of a two-dimensional coordinate system, the coordinate system having two axes which are mutually perpendicular, one of the axes being given to the thicknesses t and the other of the axes being given to the X-ray attenuation amounts μt; and
    correct the count based on the correcting data in the respective X-ray energy bins and at the respective pixels or the respective pixel areas.

22. The data processing apparatus of claim 21, wherein the processor is configured to
    approximate, with a function of the thicknesses t, the characteristic of the acquired X-ray attenuation amounts, and
    calculate, as the correcting data, correction coefficients for replacing the characteristic of the X-ray attenuation amounts μt approximated with the function with the linear target characteristic of the X-ray attenuation amounts μt corresponding to monochromatic X-rays having an X-ray energy representing the X-ray energy bins.

23. The data processing apparatus of claim 21, wherein the processor is configured to set, as the linear target characteristic, a linear line connecting an intersection and the origin, the intersection being provided by a representative thickness tr given to the object and the X-ray attenuation amount μt corresponding to the representative thickness tr, the representative thickness being set based on the plurality of mutually different thicknesses of a substance which is the same or similar in type as or to the object.

24. The X-ray apparatus of claim 21, wherein the process is configured to set, as the linear target characteristic, a linear line passing the origin and having a gradient corresponding to a linear attenuation coefficient calculated based on an X-ray effective energy or a theoretical value of a fixed X-ray energy in each of the X-ray energy bins.

* * * * *